(12) United States Patent
Fenouil et al.

(10) Patent No.: US 11,648,141 B2
(45) Date of Patent: May 16, 2023

(54) DELIVERY DEVICE, DELIVERY SYSTEM, STENT GRAFT AND A SUPPORT STRUCTURE

(71) Applicant: KARDIOZIS SAS, Aix-en-Provence (FR)

(72) Inventors: Nathalie Fenouil, Nanterre (FR); Perrine Chaffotte-Gluziki, Laxou (FR); Jean-Baptiste Pourchet, Pompey (FR)

(73) Assignee: Kardiozis SAS, Aix-en-Provence (FR)

(*) Notice: Subject to any disclaimer, the term of this patent is extended or adjusted under 35 U.S.C. 154(b) by 291 days.

(21) Appl. No.: 16/956,233

(22) PCT Filed: Dec. 19, 2018

(86) PCT No.: PCT/EP2018/085987
§ 371 (c)(1),
(2) Date: Jun. 19, 2020

(87) PCT Pub. No.: WO2019/122013
PCT Pub. Date: Jun. 27, 2019

(65) Prior Publication Data
US 2021/0315720 A1    Oct. 14, 2021

(30) Foreign Application Priority Data

Dec. 19, 2018    (WO) .................. PCT/IB2017/001750

(51) Int. Cl.
*A61F 2/966*    (2013.01)
*A61F 2/95*    (2013.01)
(Continued)

(52) U.S. Cl.
CPC ................ *A61F 2/966* (2013.01); *A61F 2/07* (2013.01); *A61F 2/9517* (2020.05);
(Continued)

(58) Field of Classification Search
CPC .......... A61F 2/966; A61F 2/07; A61F 2/9517; A61F 2/9522; A61F 2/0077;
(Continued)

(56) References Cited

U.S. PATENT DOCUMENTS 6,858,034 B1 * 2/2005 Hijlkema .................. A61F 2/95
623/1.11
6,911,039 B2    6/2005 Shiu et al.
(Continued)

FOREIGN PATENT DOCUMENTS

EP    0 696 447 A2    2/1996
EP    1 369 098 A1    12/2003
(Continued)

OTHER PUBLICATIONS

International Search Report Corresponding to PCT/EP2018/085987 dated May 24, 2019.
(Continued)

*Primary Examiner* — Yashita Sharma
(74) *Attorney, Agent, or Firm* — Finch & Maloney PLLC

(57) ABSTRACT

A delivery device (1) for an endoprosthesis (2). The endoprosthesis (2) is preferably an endoprosthesis for treating an aneurysm. The delivery device (1) comprises an outer sheath (3) and an inner tube (4). The inner tube (4) is arranged within the outer sheath (3) and at least one restraining tube (5, 30). The restraining tube (5, 30) is for holding the endoprosthesis (2) in a compressed configuration. The restraining tube (5, 30) is arranged between the outer sheath (3) and the inner tube (4). The outer sheath (3), the inner tube (4) and at least one restraining tube (5, 30) are coaxial. The restraining tube (5, 30) includes at least one axial elongation (6) extending from a distal end portion of the restraining tube. The at least one axial elongation (6) is adapted to be laced through portions of the endoprosthesis (2).

19 Claims, 18 Drawing Sheets

(51) Int. Cl.
*A61F 2/07* (2013.01)
*A61F 2/00* (2006.01)

(52) U.S. Cl.
CPC .......... *A61F 2/9522* (2020.05); *A61F 2/0077* (2013.01); *A61F 2002/075* (2013.01); *A61F 2002/9665* (2013.01); *A61F 2210/0014* (2013.01); *A61F 2220/005* (2013.01); *A61F 2220/0058* (2013.01); *A61F 2220/0075* (2013.01)

(58) Field of Classification Search
CPC ........ A61F 2002/075; A61F 2002/9665; A61F 2210/0014; A61F 2220/005; A61F 2220/0058; A61F 2220/0075; A61F 2/2436; A61F 2002/0086; A61B 17/1215; A61B 17/12113; A61B 17/12172; A61B 2017/12054
See application file for complete search history.

(56) References Cited

U.S. PATENT DOCUMENTS

| | | | |
|---|---|---|---|
| 7,160,218 B2 | 1/2007 | Greenberg et al. | |
| 7,160,318 B2 | 1/2007 | Greenberg et al. | |
| 7,264,632 B2 | 9/2007 | Wright et al. | |
| 2001/0003801 A1 | 6/2001 | Strecker | |
| 2003/0074045 A1 | 4/2003 | Buzzard et al. | |
| 2005/0273155 A1 | 12/2005 | Bahler et al. | |
| 2006/0184226 A1* | 8/2006 | Austin | A61F 2/95 623/1.11 |
| 2008/0208312 A1 | 8/2008 | Kwitkin et al. | |
| 2010/0268315 A1 | 10/2010 | Glynn et al. | |
| 2011/0270372 A1 | 11/2011 | Argentine | |
| 2011/0282425 A1 | 11/2011 | Dwork | |
| 2013/0184658 A1 | 7/2013 | Duncan | |
| 2015/0026544 A1 | 1/2015 | Barr et al. | |
| 2015/0148894 A1 | 5/2015 | Damm et al. | |
| 2015/0265444 A1* | 9/2015 | Kitaoka | A61F 2/966 623/1.11 |

FOREIGN PATENT DOCUMENTS

| | | |
|---|---|---|
| EP | 1 923 024 A2 | 5/2008 |
| EP | 2 161 009 A1 | 3/2010 |
| EP | 1 608 293 B1 | 6/2015 |
| WO | 00/71059 A1 | 11/2000 |
| WO | 2005/034811 A1 | 4/2005 |
| WO | 2010/027485 A1 | 3/2010 |

OTHER PUBLICATIONS

Written Opinion Corresponding to PCT/EP2018/085987 dated May 24, 2019.
International Search Report Corresponding to PCT/IB2017/001750 dated Oct. 11, 2018.
Written Opinion Corresponding to PCT/IB2017/001750 dated Oct. 11, 2018.

* cited by examiner

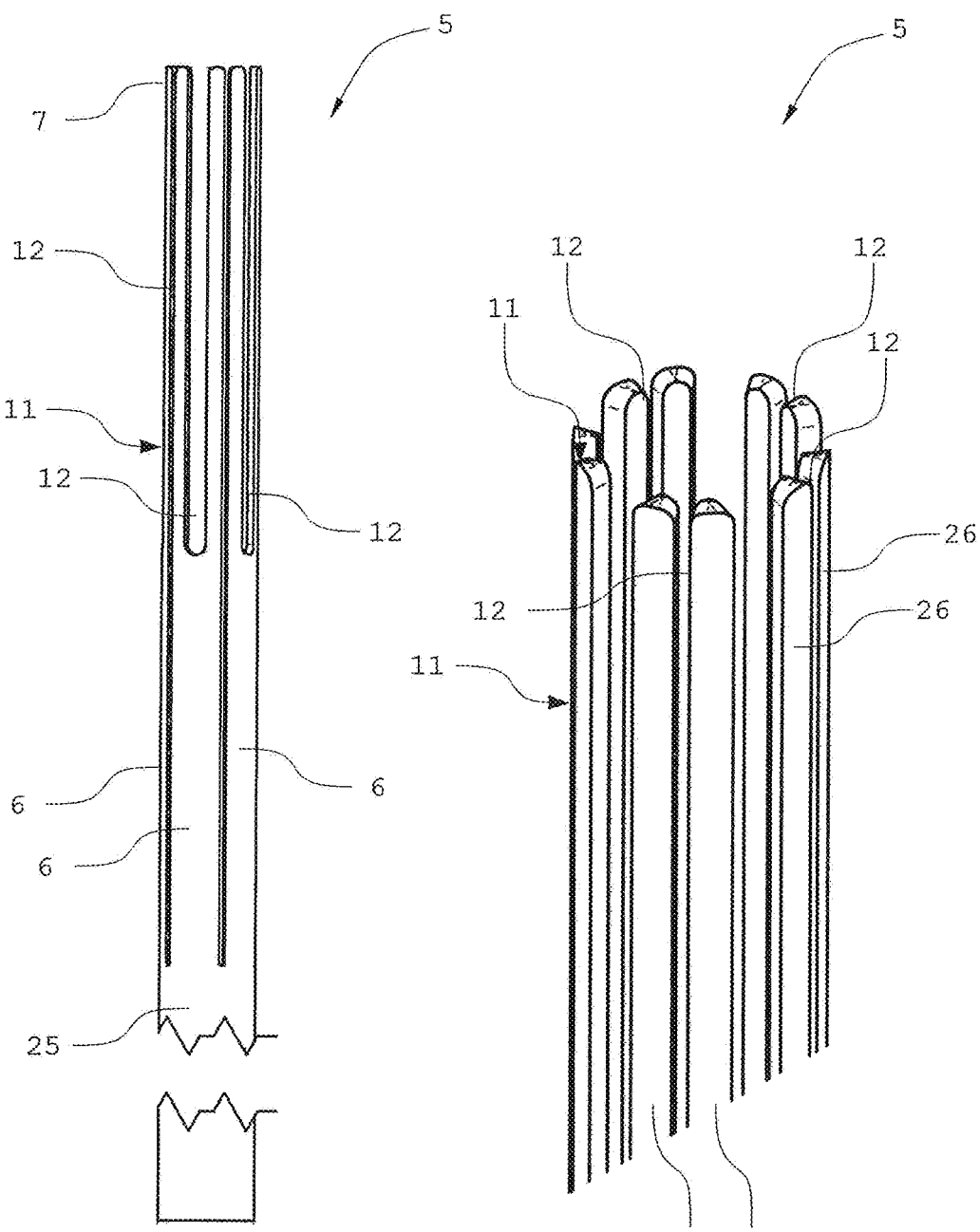

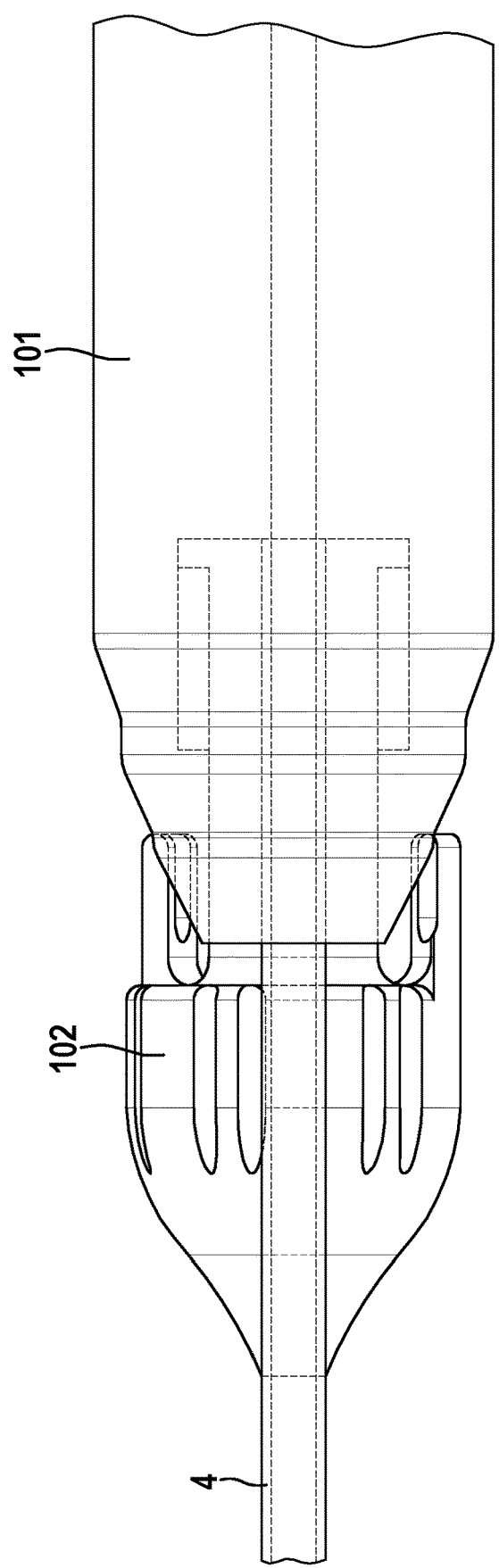

DELIVERY DEVICE, DELIVERY SYSTEM, STENT GRAFT AND A SUPPORT STRUCTURE

The present invention relates to a delivery device, a delivery system, a stent graft and a support structure according to the preambles of the independent claims.

In particular, the present invention concerns devices used for the treatment of vascular aneurysms. Vascular aneurysms are the result of abnormal dilatation of a blood vessel, usually resulting from disease and or genetic predisposition. The disease and/or genetic predisposition weakens a wall of the blood vessel and allows the wall to expand outwardly thereby forming a bulge. While aneurysms could occur in any blood vessel, they are most common in the aortic arch, the abdominal aorta and the iliac arteries. The majority of aortic aneurysms occur in the abdominal aorta, usually beginning below the renal arteries and often extending into one or both of the iliac arteries.

Aneurysms may be treated by inserting an endoprosthesis such as a stent graft into the dilated vessel. The stent graft is anchored above dilated part of the vessel and comprises a graft which bypasses the dilated vessel. This stent graft may be implanted with a catheter in a minimally invasive procedure.

U.S. Pat. No. 7,160,318 B2 discloses a modular stent graft assembly for repairing a ruptured abdominal aorta aneurysm. The assembly can be selected from an inventory containing a set of delivery systems of four sizes of aortic extend grafts and a set of delivery systems of four sizes of iliac section grafts, that accommodate a large majority of aneurysm size and delivery systems.

During the implantation of stent grafts a controlled release is preferable, in order to ensure a proper positioning of the stent graft at the implantation site.

U.S. Pat. No. 7,264,632 B2 suggests a controlled stent graft deployment delivery system. The delivery system comprises a cap coupled to a distal end of an inner tube. The cap is configured to retain at least a portion of a proximal portion of its stent graft in a radial compressed configuration. Upon a controlled axial movement between an outer tube and the inner tube and therefore the cap, the proximal end of the stent graft is released from the cap and allowed to expand. The whole system is relatively complicated and the cap has to be pushed distally in order to release the stent graft.

One object of the invention is to overcome the disadvantages of the prior art and in particular to provide a reliable delivery device, which is easy to handle and allows a precise and simple placement of the endoprosthesis.

Herein, the directions proximal and distal with regard to the delivery device are defined in reference to an operator, in particular a medical professional operating the delivery device. Proximal is a direction pointing towards the operator. Distal is a direction pointing away from the operator.

With regard to the endoprosthesis the directions are defined in regard to a patient, in which the endoprosthesis is implanted. Proximal is then defined as a direction pointing towards a centre of the body, i.e. a direction towards the heart of the patient. Distal is a direction pointing away from a centre of the body i.e. away from the heart of the patient. Depending on the mode of implantation, e.g. trans-apical or trans-femoral, the terms proximal and distal may refer to opposite directions with respect to the endoprosthesis as compared to the delivery device.

It is suggested to provide a delivery device for an endoprosthesis. The endoprosthesis is preferably an endoprosthesis for treating an aneurysm. The delivery device comprises an outer sheath and an inner tube arranged within the outer sheath. The device further comprises at least one restraining tube. The restraining tube is adapted to hold the endoprosthesis in a compressed configuration. The restraining tube is arranged between the outer sheath and the inner tube. The outer sheath, the inner tube and the at least one restraining tube are coaxial. The restraining tube includes at least one axial elongation extending from a distal end portion of the restraining tube. The at least one axial elongation is adapted to be laced through portions of the endoprosthesis.

Compressed configuration as used herein includes partially compressed (i.e. partially expanded) and fully compressed configurations. When the endoprosthesis is fully released from the delivery device it assumes an expanded configuration.

The delivery device is particularly suited for stent grafts for treating aneurysms. The delivery device is also suited for other endoprosthesis such as stented heart-valves.

With such a device, the endoprosthesis may be held in the compressed configuration by the axial elongations without requiring a complex mechanism. When the outer sheath is withdrawn, the endoprosthesis will be kept in a (partially) compressed configuration by the at least one restraining tube. In such a configuration, the position of the endoprosthesis might be easily adjusted to ensure a proper positioning at the implantation site. In the compressed configuration, the endoprosthesis does preferably not contact the vascular wall in order to not irritate any tissue during a potential repositioning. The endoprosthesis can then be released and allowed to expand by withdrawing the restraining tube. When the restraining tube is withdrawn, the axial elongation is withdrawn from the portion and therefore not laced anymore through the portion. Therewith, no compression force is acting on the endoprosthesis and the endoprosthesis is allowed to (fully) expand.

The device may further comprise a handle portion. The restraining tube may extend to such a handle portion. The distal end portion of the handle may be a distal end of the restraining tube. A handle portion allows an easy and reliable withdrawing of the restraining tube(s) and therefore allows reliable, controlled expansion of the endoprosthesis.

The elongations are preferably integrally formed with the rest of the restraining tube. Integrally formed restraining tubes provide a simple and cost effective variant of restraining tubes. Alternatively, the elongations might be coupled to the rest of the restraining tubes, e.g. through gluing or moulding.

The inner tube, the outer sheath and the distal tip may comprise or be made of a plastic material. Exemplary materials for suitable plastics are Pebax, PEEK and PTFE. Alternatively, other biocompatible materials such as metal (alloys) might be used.

In a preferred embodiment, the at least one restraining tube includes multiple elongations. The multiple elongations extend from the distal end portion of the restraining tube. Preferably, the restraining tube comprises two or three or four or five or more elongations. The endoprosthesis may be held in the compressed configuration at multiple portions. Thus, the endoprosthesis can be held more stably with such an arrangement. The elongations may be distributed, preferably evenly, along the circumference of the restraining tube.

A further aspect of the invention relates to a catheter with an inner tube and a tip. The tip may form a cavity that extends from a proximal side in a distal direction and a member, preferably a harpoon member is arranged slidably in the cavity. The member may be suitable for holding a stent in compressed configuration in a first position and release the stent in a second position. The member may be tubular and arranged slidably on the inner tube. The member may be arranged partly, preferably only partly, in the cavity. The cavity may have an entry that is smaller in cross-section than the cavity and/or the cavity may be at least partly radially offset to the entry. Thereby, with a suitably formed member, the member can be slidably retained, while the member cannot be lost.

In one embodiment, the restraining tube comprises a harpoon member with a base and an arm extending from the harpoon member. The base and arm may be adapted to receive the stent in a gap formed in between base and arm. The gap may be closed by the tip, in particular a proximal extension from the tip. The harpoon member may be held slidably by the tip. The base of the harpoon member may comprise a flange. The flange may be slidably retained by a cavity in the tip. The harpoon member may integrally formed with a handle portion connecting part or may be formed as a separate part.

The harpoon member may be held in a cavity formed between the proximal extension of the tip and the inner tube. The arm may extend along a longitudinal direction of the catheter. The arm of the harpoon member is laced through an opening in the stent.

The cavity may have an entry with a smaller cross-section than the cavity. The entry may have a smaller cross-section than at least a part of the base. The harpoon member may have a tubular form and may include one or more arms, in particular three, four five or six arms or more extending from it.

A proximal side of the harpoon member may be inclined. The proximal side of the harpoon member may have rounded edges. Thereby, the walls of a vessel of a patient are protected from injury, in particular from the edges of the tip or the harpoon member itself.

In a preferred embodiment, the device comprises a distal tip. The distal tip is attached to a distal end of the inner tube and comprises at least one recess. The at least one recess is adapted to receive at least one of the elongation(s) of a restraining tube.

The recess preferably extends circularly around the distal tip. The recess preferably extends from a proximal side of the tip in a distal direction. The recess may be adapted to receive the elongations of one or two or more restraining tubes. Preferably, the recess is adapted to receive all of the elongations of the restraining tubes, if there are multiple. The recess holds the restraining tube in place, i.e. with the extension laced through the portion and therewith prevents the endoprosthesis from separation. The recess therefore aids to hold the endoprosthesis in the compressed delivery portion. Upon moving the restraining tube, the restraining tube is then withdrawn from the recess and the endoprosthesis is deployed.

In a preferred embodiment, the at least one restraining tube is releasably engageable to the distal tip by engagement of at least one of these elongations in one of the at least one recess of the proximal tip. Thereby, the elongations may be held securely to the distal tip.

The device may comprise a first and a second restraining tube, preferably only the first and the second restraining tube and the distal tip a first recess and a second recess. Preferably, both recesses extend circularly around the distal tip. The first recess is adapted to receive at least one of the elongation(s) of the first restraining tube. The second recess is adapted to receive at least one of the elongation(s) of the second restraining tube. Thereby, two restraining tubes can be held in the distal tip by separate recesses.

In order to implant the endoprosthesis, both restraining tubes are withdrawn such that the endoprosthesis is no longer compressed by the restraining tubes. Therewith, the endoprosthesis is allowed to expand.

In a preferred embodiment, the delivery device comprises exactly two restraining tubes.

The first restraining tube might be laced through an opening on the proximal portion of the endoprosthesis; the second restraining tube might be laced through a distal portion of the endoprosthesis. Therewith, the whole endoprosthesis is reliably kept compressed and secured to the delivery device.

The second recess preferably extends from a proximal side of the tip in a distal direction. The second recess is preferably adapted to receive all of the elongations of the second restraining tube. The second recess in the distal tip may be positioned radially outwards in relation to the first recess.

In a preferred embodiment, at least one of the elongations includes at least one attachment element adapted to be engaged with a corresponding element of the endoprosthesis. Preferably, each elongation comprises such an attachment element. Preferably, the attachment element is a slot extending from a distal end of the axial elongation(s). The slot(s) may have a length of 5 to 15 mm. In a preferred embodiment, they have a length of 8 to 12 mm, particularly preferred about 10 mm.

Preferably, each elongation comprises one attachment element. The corresponding element is preferably an anchor pin. Thereby, the endoprosthesis may be fixed to the restraining tube a precise location, which enables a precise placement of the endoprosthesis.

Preferably, the corresponding element is arranged at the portion. The elongation is laced through the portion and the corresponding element can directly engage the attachment element of the elongation. With a slot and a pin, a rotational secured position can be achieved. Further, with a slot having an end adapted to be brought into contact with the pin, the relative axial position in one direction between elongation and the endoprosthesis is also secured.

In a preferred embodiment, the first restraining tube is adapted to be laced through a proximal portion of the endoprosthesis, in particular through proximal arches. Thereby, a proximal portion of the endoprosthesis can be held.

Alternatively, the first restraining tube is adapted to be laced through a proximal portion of the endoprosthesis, in particular through proximal arches. Thereby, a proximal portion of the endoprosthesis can be held.

In one embodiment, a second restraining tube is adapted to be laced through a distal portion of the endoprosthesis. In a preferred embodiment, the second restraining tube is adapted to be laced through a proximal part of a graft of the endoprosthesis, in particular through a repositioning hole at the proximal part of the graft. Thereby, a distal portion of the endoprosthesis may be held by the delivery device. This facilitates repositioning the endoprosthesis during implantation.

With a first and a second restraining tube laced through a proximal and a distal portion, respectively, the whole endoprosthesis can reliably be kept compressed.

In a preferred embodiment, the first and the second restraining tube each include multiple elongations extending from their respective distal end portions. The elongations of the second restraining tube are longer in an axial direction of the restraining tubes than the elongations of the first restraining tube. Thereby, the axial elongations of the second restraining tube can be laced through a distal portion of the endoprosthesis and attached to a distal part, preferably a distal tip, of the delivery device. The shorter elongation(s) can be laced through a proximal portion and therewith allowing a reliable compression of the endoprosthesis. The distal portion of the endoprosthesis may be a distal portion of a stent or a distal or proximal portion of a graft.

In a preferred embodiment, the first restraining tube is at least partially arranged within the second restraining tube. At least a proximal part of the first restraining tube may be arranged within the second restraining tube. Further, the elongations of the second restraining tubes may be at least partially arranged within the elongations of the first restraining tube. Thereby, the two restraining tubes use less space and the engaged endoprosthesis may be compressed to a smaller delivery state.

In a preferred embodiment, the elongations comprise or made of a biocompatible material. Preferred materials are in particular a metal and/or plastic. Particularly preferred materials are stainless steel (inox) or a nickel titanium alloy such as nitinol or PEEK or a chrome cobalt alloy.

According to another aspect of the invention, it is suggested to provide a delivery system comprising a delivery device as described hereinabove and an endoprosthesis. The endoprosthesis comprises a stent. The elongation(s) of at least one of the restraining tubes is laced through a portion of the endoprosthesis.

The endoprosthesis may be self-expandable. Therewith, a withdrawal of the retaining tube will directly result in an expansion to the desired shape.

In particular, the delivery device comprises multiple elongations which are laced through portions of the stent.

By engaging the stent, which forms a relatively rigid part, a reliable compression of this portion of the endoprosthesis can be achieved through the lacing of the elongations.

In a preferred embodiment, the stent comprises arches, which are formed by struts. The elongations of a first restraining tube are laced through arches of the stent. The arches are preferably arranged at a proximal end of the endoprosthesis. Thereby, the proximal end of the endoprosthesis may be securely held. The arches might also be formed at another portion of the stent such as the distal portion. The elongations may be laced through an end portion of the endoprosthesis, which is closest to the distal tip of the delivery device.

The end of the endoprosthesis through which the elongations are laced may depend on the delivery approach. In a retrograde approach the elongations may be laced through a proximal end of the in the prosthesis. In an antegrade approach the elongations may be laced through a distal end of the endoprosthesis.

In a preferred embodiment, the endoprosthesis comprises a graft. The elongations of the second restraining tube are laced through the graft of the endoprosthesis. The graft is preferably arranged at least partially distally to the stent. The elongations are preferably laced through pre-formed openings formed in the graft. Alternatively, the elongations may be laced directly through the graft thereby forming the openings. A distal portion of the endoprosthesis may therewith be kept compressed and precisely placed. Further the endoprosthesis may be repositioned as long as the second restraining tube is engaged.

In a preferred embodiment, the elongations of a first and/or a second restraining tube are laced through struts of the stent forming a ring. The ring may extend radially inwardly from the stent or the graft or a second stent in the graft. A lacing through a ring of a stent provides a reliable securing of the stent to the restraining tube and therewith a reliable compression.

The lacing trough the ring might be in addition to the lacing through the graft and/or arches as described hereinbefore.

In a preferred embodiment, the elongations of a second restraining tube are laced through a distal part of the endoprosthesis. Alternatively, they might be laced through another portion i.e. a middle or the proximal portion.

In a preferred embodiment, the stent includes at least one anchor pin. The delivery device includes at least one elongation, wherein the at least one of the elongation(s), preferably each elongation, comprises one or more slots. At least one of the slots is operatively engaged or engageable with the at least one anchor pin.

Therewith, a position of the endoprosthesis can reliably be secured as described hereinbefore.

In a preferred embodiment, one or more anchor pins are arranged at an apex, preferably a proximal apex, of the arches. Preferably, the apex forms a proximal end of the endoprosthesis. Preferably, each apex comprises at most one anchor pin. Preferably, the anchor pin is arranged at a proximal end of the endoprosthesis.

In addition to or alternatively to the engagement with slot(s) of the elongations, the endoprosthesis pins might facilitate anchoring of the endoprosthesis to a wall of a body vessel by engaging the tissue.

In a preferred embodiment, the endoprosthesis includes an outer cover, preferably a graft. The outer cover covers a part of a stent ring. The stent ring comprises at least one repositioning opening. An elongation of at least one restraining tube is laced through the at least one repositioning opening. If a second restraining tube is present, the elongations of the second restraining tube are preferably laced through the repositioning opening. Thereby, while withdrawing the outer sheath the distal portion of the endoprosthesis is more compressed than the proximal portion. This facilitates a repositioning of the endoprosthesis at least in the distal direction.

The outer cover may be realized as a graft. The repositioning opening may be realized as a repositioning hole. The repositioning opening is preferably at a proximal part of the cover. Particularly preferred, the opening is provided by the stent. Thereby, high positioning accuracy is achieved by preventing elastic recoil of the stent of the graft. Such a repositioning opening is advantageous for a heart valve or a thoracic endoprosthesis.

In one embodiment the repositioning opening may be disposed at a distal end portion of the stent. The repositioning opening may be disposed distally of the distal edge of the cover. Such a repositioning hole is advantageous for abdominal endoprosthesis.

One object of the invention is to provide a delivery device, which allows a secure release of an endoprosthesis and prevents a user from accidentally releasing the endoprosthesis.

According to another aspect of the invention, it is suggested to provide a delivery device for an endoprosthesis comprising a handle portion. The handle portion comprises a body, a first gripping portion for retracting an outer sheath of the delivery device, and a separate second gripping portion for retracting the outer sheath. The first gripping portion comprises a ring, wherein said ring is rotatable around a longitudinal axis of the body such that upon rotation of the ring the outer sheath is withdrawn. The separate second gripping portion is axially connected or connectable to the outer sheath. The second gripping portion is slidable relatively to the body along the longitudinal axis of the body such that the other sheath is retractable by pulling the second gripping portion longitudinally.

The ring may also be open and in particular C-shaped. Herein, connected is to be understood as directly or indirectly connected.

With such a device, the other sheath may be retracted at a slow controlled mode, by rotating the first gripping portion and in a fast mode with the second gripping portion. Since the two gripping portions are separated, a risk of an accidental use of the non-intended gripping portion is minimized.

In a preferred embodiment, the handle portion comprises an inner connecting member. The inner connecting member is rotatably connected or connectable to the second gripping portion and connected or connectable to the outer sheath. The inner connecting member may be cylindrical, in particular tubular. The inner connecting member may be freely rotatable connected to the second gripping portion such that rotation of the inner connecting member does not result in a rotation of the second gripping portion. This allows a slow retraction with the first gripping portion and a rotation of the inner connecting member without a rotation of the second gripping portion.

In a preferred embodiment, the inner connecting member comprises one or two or more cam(s). The cam(s) extend(s) radially outwardly. The cam(s) is/are engageable in a circumferential recess of the second gripping portion. Alternatively the one or two or cam(s) extend(s) radially inward from the second gripping portion and is/are engageable on a circumferential recess of the inner connecting member. Thereby, the inner connecting member may be connected freely rotatable to the second gripping portion such that rotation of the inner connecting member does not result in a rotation of the second gripping portion. At the same time, axial forces are transmitted from the second gripping portion to the inner connecting member. The proposed connection(s) allow a low friction, easy to produce and reliable connection.

In a preferred embodiment, the inner connecting member is rotatably (i.e. freely rotatable) connected or connectable to the outer sheath. Thereby, a rotation of the inner connecting member does not result in a rotation of the outer sheath.

In a preferred embodiment, the inner connecting member is tubular with an inner lumen. The inner lumen comprises a circumferential recess for receiving a cam of the outer sheath. Alternatively one or two or more cams extend into the inner lumen for rotatably attaching the outer sheath to the inner connecting member. Thereby, a rotatable connection may be formed between the inner connecting member and the outer sheath.

The rotatable connection allows a transfer of axial forces from the handle portion to the outer sheath, while torsional moments are not transferred. Alternatively to the above described cams of the outer sheath, the outer sheath may comprise a radially inwardly extending recess.

In a preferred embodiment, the second gripping portion comprises a tubular outer connecting member. The outer connecting member is slidably arranged on a, preferably threaded, tube. Thereby, the second gripping portion may slide along the longitudinal axis of the handle portion.

By sliding the outer connecting member, the outer sheath may be withdrawn without rotation of the tube in the fast mode. The outer sheath can be withdrawn faster than through rotation of the first gripping portion.

In a preferred embodiment, the handle portion comprises a threaded tube. The threaded tube is disposed between a second gripping portion and the inner connecting member. The second gripping portion is connected or connectable to the inner connecting member through axially extending slotted holes in the threaded tube.

Preferably, the inner connecting member is connected to the outer connecting member with cams. Thereby, the inner connecting member and the outer sheath are connected to the second gripping portion, allowing a transfer of axial forces from the second gripping portion to the outer sheath.

In a preferred embodiment, the first and second gripping portion may be releasably coupled. Thereby, when actuating the second gripping portion, the first gripping portion may be uncoupled and does not move (i.e. no rotation) when the second gripping portion slides. This reduces the resistance (i.e. friction losses) when actuating the second gripping portion and improves the ease of use. The same may apply vice versa for the first gripping portion.

In a preferred embodiment, the first or second gripping portion comprises a selection mechanism. The selection mechanism comprises a selection element, preferably a button. The selection element is moveable between an open position and a locked position. In the locked position the second gripping portion is directly or indirectly engaged to the first gripping portion such that the outer sheath is retractable by rotating of the first gripping portion. In the open position the second gripping portion is released from the first gripping portion such that the outer sheath is retractable by pulling the second gripping portion longitudinally relatively to the body.

The selection element is preferably biased towards the locked position. The bias is preferably achieved with a spring connected to the body and the button.

In one embodiment the locked and the open position of the button may be identical (e.g. a monostable switch for toggling between locked and open position).

Thereby, a desired mode of use, i.e. fast (through pulling) or slow (through rotation), may be chosen by the operator. For example, during an implantation procedure of an endoprosthesis first the first gripping may be rotated and the outer sheath may be retracted relatively slowly, allowing a precise placement and potential adjustments. Once an end of the endoprosthesis is precisely placed, the endoprosthesis may be released with the selection mechanism in the open position allowing a faster withdrawal of the outer sheath and therefore a fast release of the endoprosthesis from the outer sheath.

In a preferred embodiment, the handle portion comprises a threaded tube, which is disposed radially inwardly in relation to the second gripping portion. In a preferred embodiment the handle portion includes only one threaded tube allowing a simple setup. The threaded tube is preferably hollow. The threaded tube is aligned coaxially with the body of the handle portion. The second gripping portion is indirectly engaged to the first gripping portion via the threaded tube in the locked position and released from the threaded tube and the first gripping portion in the open position. Thereby, the first and second gripping portion may be easily coupled and decoupled depending on the desired mode of use.

In a preferred embodiment, the threaded tube is fixedly connected to the first gripping portion or integral with the first gripping portion. Thereby, a rotation of the first gripping portion is transferred to the threaded tube and transformed to an axial movement of the outer sheath.

The threaded tube may be held rotably relatively to the body. The first gripping portion may be in a fixed longitudinal position (i.e. no sliding along the longitudinal direction of the body). This results in a more clearly arranged device.

Alternatively, the first gripping portion may comprise an inner threading, which is operatively engaged to the threaded tube. Through rotation of the first gripping portion, the threaded tube is moved axially. Preferably, the threaded tube is not rotatable. Thereby, the threaded tube and the second gripping portion in the locked position may be moved in an axial direction upon rotation of the first gripping portion.

In a preferred embodiment, the second gripping portion comprises one or two or more radially moveable contact element(s). The threaded tube comprises an outer threading. The contact element(s) is/are adapted to engage the outer threading in the locked position and is/are released from the outer threading in the open position. Thereby, the second gripping portion may be coupled to or released from the first gripping portion depending on the desired mode of use.

In a preferred embodiment, the one or two or more contact element(s) comprise(s) or is/are made of wire. Preferably, the wire is a plastic or metal wire, in particular a steel wire. The thickness of the wire may be smaller than a thread of the outer threading. The wire may be L-shaped or U-shaped. The wire may comprise one or two end portions at which it may be attached to the second gripping portion. The wire may be moveable partly or entirely radially to the threaded tube.

The wire provides a reliable solution to engage the second gripping portion with the outer threading.

In a preferred embodiment, the tubular outer connecting member comprises one or two or more radially extending through hole(s). The one or two contact element(s) is/are disposed at least partially in the one or two or more through hole(s). Thereby, the selection element may be easily and reliably connected to the outer threading with the contact element.

In a preferred embodiment, the selection element comprises a radially moveable button. The button is operatively attached to the moveable contact element(s). Preferably, the button is fixedly attached to the moveable contact element(s). The second gripping portion comprises a socket for holding the button. The socket may comprise an inner cut-out for the button. A length of the cut-out is shorter than a length of the button along an axial direction of the handle portion. Thereby, the button is securely held in the second gripping portion. Another advantage is that a radially outward movement of the button is limited by the shorter cut-out and that button is thereby secured to the rest of the handle portion. By pressing the button, the contact elements are released from the threading thereby allowing a free sliding of the second gripping portion on the tube.

In a preferred embodiment, the contact elements, which are fixedly attached to the button, form a stopper for the button. Thereby, radially outward movement of the button may be limited. Thereby, the button is secured to the rest of the handle portion.

In a preferred embodiment of all devices described hereinbefore, a handle portion comprises at least one release mechanism for releasably fixing a restraining tube to the handle portion. Each release mechanism comprises a release element, preferably a button or lever, which is moveable between an open and a locked position. The release element is preferably biased towards the locked position. Preferably, the release element is biased by a release spring. In the locked position the restraining tube is fixedly connected to the body of the handle portion. In the open position the restraining tube is adapted to be axially slid longitudinally in relation to the body of the handle portion by retracting the restraining tube. Thereby, the restraining tube(s) may be fixedly attached to the body of the handle portion and may be released from the handle portion, when needed. The device may comprise a first and/or a second restraining tube.

The release mechanism may also be combined with a delivery system as described herein above.

Such a design prevents that the restraining tube(s) is/are unintendedly withdrawn. In the locked position, the restraining tubes cannot be withdrawn. Once the endoprosthesis is at the desired location, the release mechanism is moved into the open position allowing withdrawal of the restraining element and therefore expansion of the endoprosthesis.

In a preferred embodiment, the handle portion comprises two release mechanisms for releasably fixing a first and second restraining tube. Thereby, two restraining tubes can be held by the handle portion. The release mechanisms may be arranged at a distal end portion of the handle portion. Preferably, the release mechanisms are arranged distally of the second gripping portion. Preferably, a first release mechanism is arranged distally of a second release mechanism. The distal arrangement allows a comfortable activation, as the mechanisms are not too close to the body of the operator.

In a preferred embodiment, the handle portion and a restraining tube are connected by an actuation spring. The actuation spring is pre-stressed in a longitudinal direction of the handle portion such that upon opening the release mechanism the restraining tube is retracted by the pre-stressed actuation spring. Thereby, an operator, i.e. a medical professional, only needs to actuate the release element to automatically withdraw the restraining tube. This allows a fast and easy withdrawal of the restraining tube.

In a preferred embodiment, the release mechanism comprises a stopper, preferably a ring, arranged to prevent moving the recess mechanism from the locked position the open position. The stopper is preferably disposed proximally to the release mechanism. The stopper prevents accidental movement of the release mechanism into the open position and therefore accidental axial movement of the restraining tube. To allow activation of the release mechanism, the stopper has to be actively moved away from the release mechanism. The ring may be open, for example C-shaped. Thereby, the stopper may be removed from the handle portion.

In a preferred embodiment, the second gripping portion is disposed proximally of the first gripping portion. After rotation of the first gripping portion, the operator may pull the second gripping portion arranged closer to him. This is a more ergonomic mode of operation.

In a preferred embodiment, the body comprises a third gripping portion. The third gripping portion may not take part in the movement of the outer sheath and allows the operator to hold handle without the risk of unintentional movement. Hence, the handle portion can be securely carried without accidentally retracting the outer sheath.

The first and second gripping portion may be axially separated, in particular in an unretracted configuration of the outer sheath. This reduces a risk of accidentally actuating the second gripping portion.

In a preferred embodiment, the third gripping portion is disposed between the first and the second gripping portion along a longitudinal direction of the handle portion. This position has been found to be comfortable for the operator. Further, when actuating the first gripping portion, there no risk of accidentally actuating the second gripping portion.

In preferred embodiment, the body comprises one or two or more axially extending slotted hole(s). The second gripping portion is at least partially arranged slidably in the slotted hole(s).

Another object of the invention is providing a stent graft, which allows a simple loading procedure.

It is suggested to provide a stent graft, preferably for treating an aneurysm, with a collapsible and a re-expandable stent. The stent is preferably a vascular or a heart stent. The stent comprises a proximal and a distal end. The stent further comprises at least one hole to receive a wire or elongation for loading the stent into a delivery device. The stent further comprises an outer cover covering a distal part of the stent. The at least one hole is disposed proximally of a proximal edge of the cover.

Wires may be laced through the at least one hole. The stent graft may be compressed into the collapsed configuration, by pulling the stent through a conical hole via the attached wires. This provides an easy solution to compress stent grafts with radially expandable stents. Further, the graft does not include holes.

In preferred embodiment, the at least one hole is disposed less than 2.5 mm proximally of the proximal edged cover. Preferably, the at least one hole is disposed between 1 mm and 2 mm proximally of the proximal edge. The arrangement allows a pulling of the stent at a location close to the cover Such an arrangement prevents a leak through the loading hole (type 1 endoleak). Further, this arrangement allows a simpler stent design.

The stent may comprise or is made of a shape memory material. Examples for shape memory materials are nickel titanium alloys such as nitinol and chrome cobalt alloys.

In a preferred embodiment, stent includes at least one pair of struts having a common apex and extending from the apex in a distal direction. The hole is disposed at the apex of the struts.

The provision of the hole at an apex allows an easy design of the stent as apexes already form circumferentially at least partly a hole.

In a preferred embodiment, the hole is formed in between the pair of struts and includes an open end formed by the pair of struts. The open end may be on a distal side of the hole.

In a preferred embodiment, the stent comprises three or four or five or more holes. Thereby, higher forces can be transmitted onto the stent graft. Further, the forces on the stent can better be distributed circumferentially avoiding any tilting of the stent.

In a preferred embodiment, the holes have the diameter of less than 1.5 mm, preferably less than 1 mm. In a particular preferred embodiment, the holes have diameter between 0.7 and 0.8 mm. The diameter of the holes may be defined by a needle which is laces a wire through the holes. By providing small holes, there is not much space between the wire and the surrounding struts allowing a reliable movement.

In one embodiment, the proximal edge of the cover may be undulating. When the proximal edge is undulating, the holes are preferably not covered by the cover.

One object of the invention is to provide a simple support structure.

According to another aspect of the invention, it is suggested to provide a support structure with thrombogenic elements for a stent graft. The support structure is sized and shaped to be mounted on the stent graft. The support structure comprises at least one strip of a fabric. A plurality of elongated thrombogenic elements, preferably fibres, are attached to the at least one strip. Thereby, a support structure may be provided independently of the stent graft and may be fabricated independently of the stent graft. The support structure is in particular separate from the stent graft. Such a support structure can be attached to the stent graft. Therewith, conventional stent grafts can be provided with thrombogenic elements, if desired.

The thrombogenic elements are in particular shaped to be released into an aneurysm. "shaped" may refer to a suitable material, thickness and/or length.

The support structure may have a length greater than the diameter of a stent graft to which the support structure is attached. The length is in particular greater than a circumference of the stent graft. This allows a fast fixation of the support structure to the stent graft. Further, this allows a preparation of the stent graft by a surgeon at the site of the operation.

In a preferred embodiment, the support structure or the endoprosthesis may comprise an attachment interface for attachment to the stent graft. The attachment interface may be formed by at least one of: hooks, ridges, a surface for adhesives, a layer of an adhesive or similar.

Thereby, the support structure may be selected for the patient. For example, according to one further aspect of the invention a set may be provided with a stent graft and a plurality of support structures. The support structures may vary in density, and/or diameter and/or length of the thrombogenic elements. Depending on the size and the structure of the aneurysm, a suitable support structure may be chosen and attached to the stent graft. A further aspect of the invention may relate to a set with a plurality of support structures as described above.

The support structure may include a first part with thrombogenic elements for endoleaks and a second part with thrombogenic elements for an aneurysm. The thrombogenic elements for the aneurysm are relatively longer. The thrombogenic elements may be denser, i.e. placed closer to each other, for the endoleak.

The thrombogenic elements may be adapted to prevent and endoleak or to treat an aneurysm.

In a preferred embodiment, the thrombogenic elements are sewed, in particular stitched, glued, welded or riveted to the at least one strip. Theses attachment methods provide a reliable attachment of the thrombogenic elements to the strip.

In a preferred embodiment, the thrombogenic elements comprise a first and a second end. The first and the second ends are both attached to the strip. Thereby, the thrombogenic elements form a loop. Thereby, with one thrombogenic fibre attached, two thrombogenic fibres are extending from the strip increasing the volume to be treated.

In a preferred embodiment, the elongate thrombogenic elements comprise a first and a second end wherein the first ends are connected to the strip and the second ends are realisably connected to one or two or more secondary strips. Therewith, the second end of the thrombogenic elements might, e.g. after implantation, be released from the secondary strip to extend further radially away from the first strip. Therewith, an interference of the thrombogenic elements during loading and implantation of the stent-graft is minimized.

In a preferred embodiment, the at least one strip, preferably all strips, is formed by threads or fibres. Such materials have been shown to be durable and biocompatible.

In a preferred embodiment, the strip(s) is/are made of a synthetic fibre. The fibre may be a poly amide (PA), PET, PE, PTFE, FEP or PFA. Such materials have been shown to be durable and biocompatible.

In a preferred embodiment, the support structure comprises only one strip. Thereby, a simple support structure can be provided.

In a preferred embodiment, the support structure comprises a plurality, preferably four, five, six, seven or more, of parallel strips. The parallel strips extend longitudinally and are transversely spaced apart. The longitudinal strips are interconnected by transversely extending strips. Thereby, the longitudinal and the transverse strips form a mesh.

In a preferred embodiment, the support structure comprises a longitudinally extending membrane, which is attached to the strips. In a preferred embodiment, the membrane is made out of or comprises a polymeric material, preferably FEP or PFA. The polymeric material may be PE, PA. Alternatively the membrane may comprise or is made of a natural material like silk.

In a preferred embodiment, the thrombogenic elements are attached to transversely outer strips, which extend longitudinally. In one embodiment the thrombogenic elements are only fixedly attached to transversely outer strips. Thereby, the mesh may be attached on either side of the mesh to a stent graft.

According to another aspect of the invention, it is suggested to provide a stent graft comprising one or more body parts with a graft, wherein one or two or more support structures are arranged on a radially outer surface of the graft.

In a preferred embodiment, the at least one support structure is sewn, glued or welded to the one or more body parts.

In a preferred embodiment, at least one support structure is wound helically around the one or more body part.

In a preferred embodiment, a longitudinal direction of at least one support structure is parallel to a longitudinal axis of the one or more body parts.

In a preferred embodiment, at least one support structure is wound circumferentially around the one or more body parts.

In a preferred embodiment, the stent graft comprises two or more body parts. A first tubular body part includes a proximal opening and two distal openings and a second tubular body part is attached to one of the distal openings. One or two or more support structures are attached to the first and/or second body part.

In a preferred embodiment, two or more support structures, preferably four to eight support structures are arranged on the outer surface of the one or more body parts. Particularly preferred two or more structures are arranged on each of the body parts.

Non-limiting embodiments of the invention are described, by way of example only, with respect to the companying drawings, in which:

FIG. 1: is a schematic drawing of a delivery device according to the invention;

FIG. 2: is a detailed view a distal portion of the delivery device according to FIG. 1;

FIGS. 3A and 3B are detailed views of a restraining tube;

Figure 6:
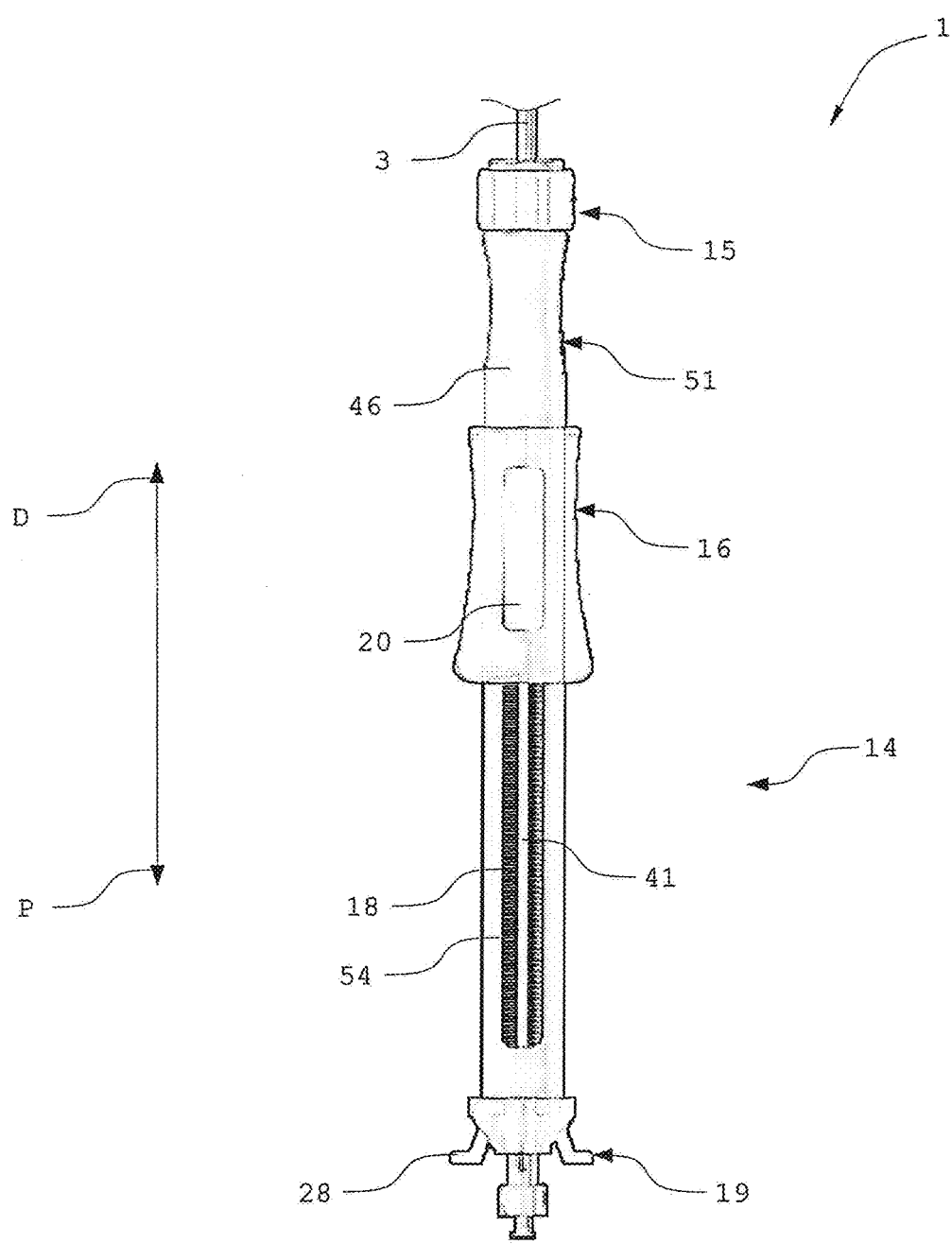
Figure 7:
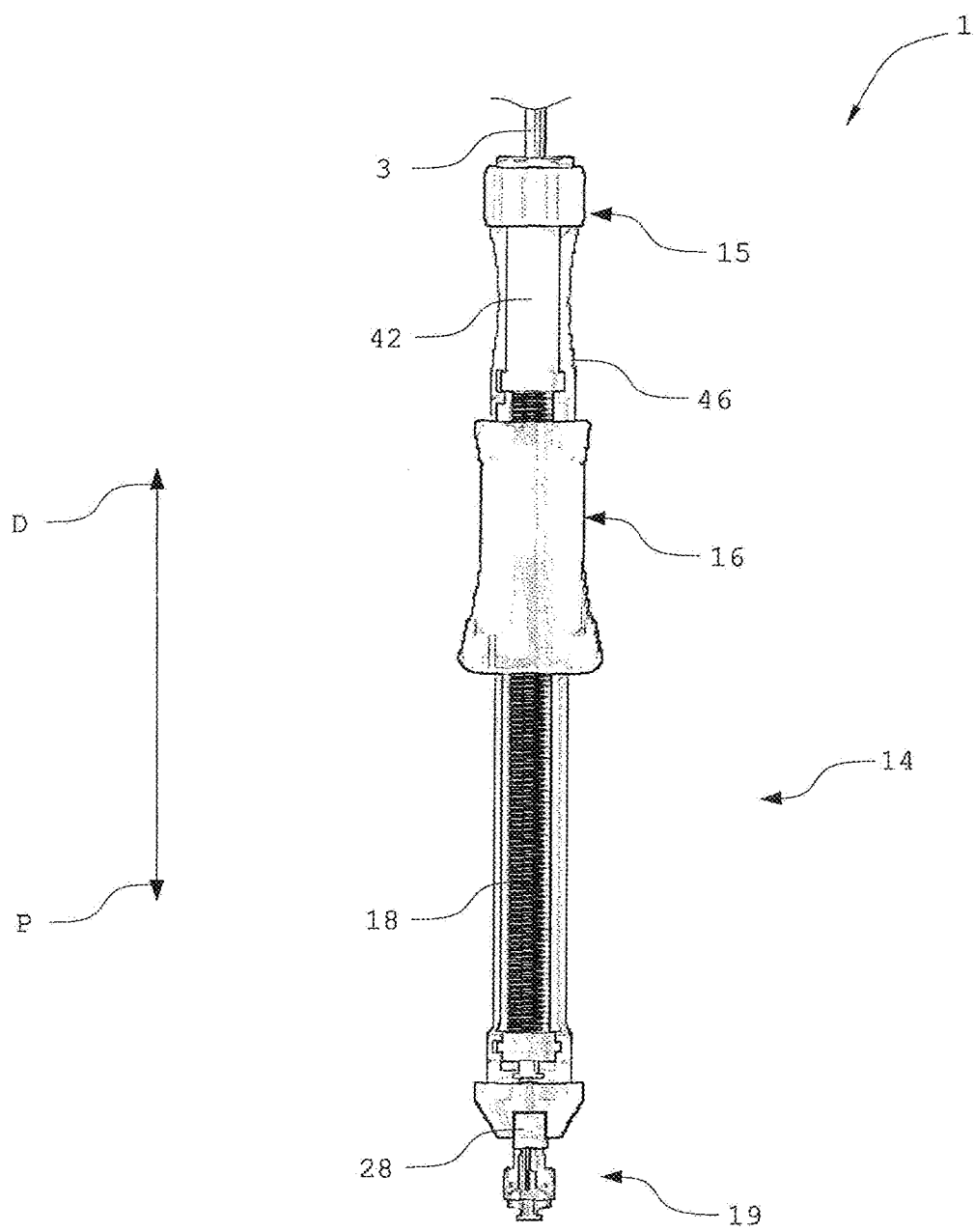
Figure 8:
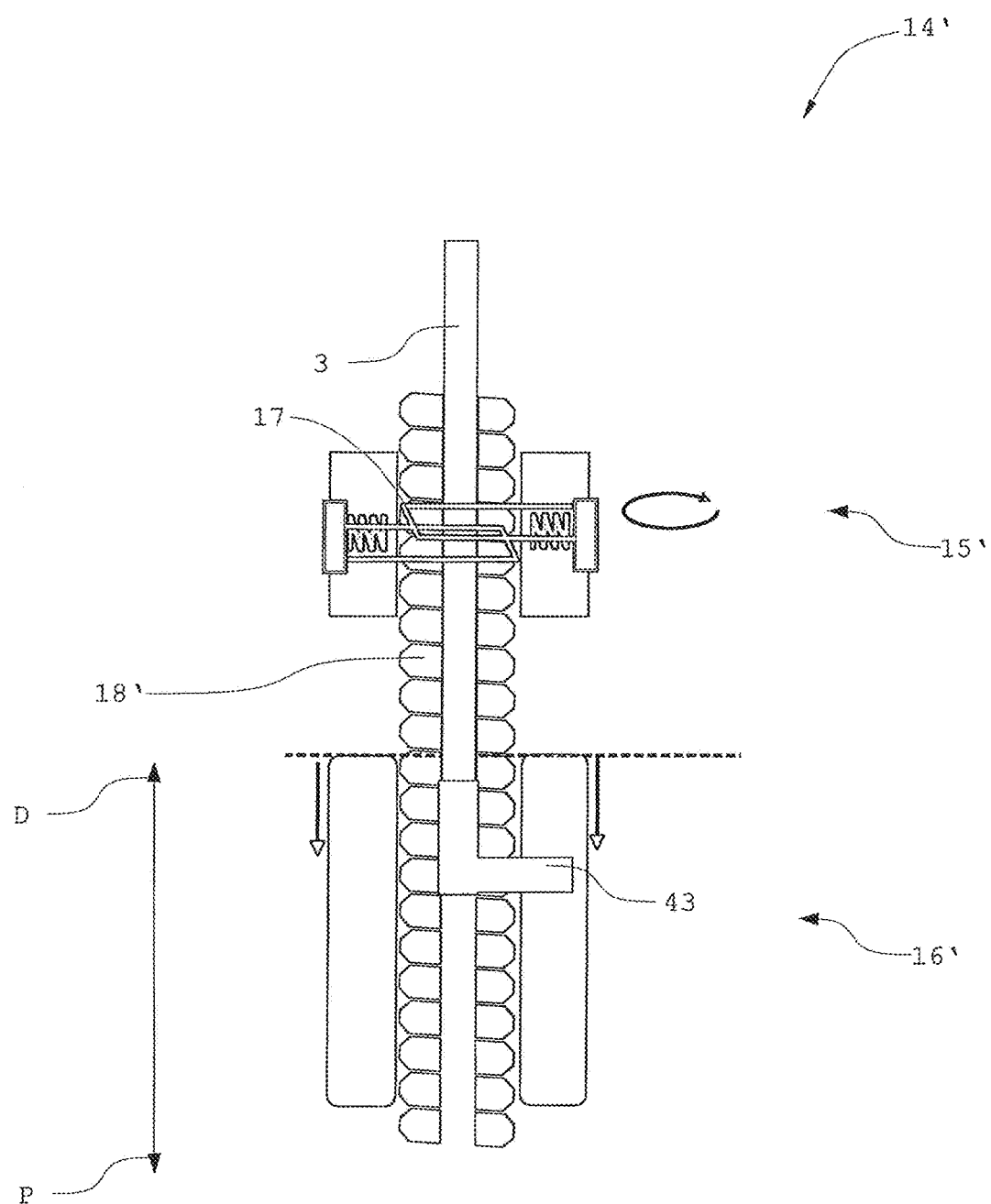
Figure 9:
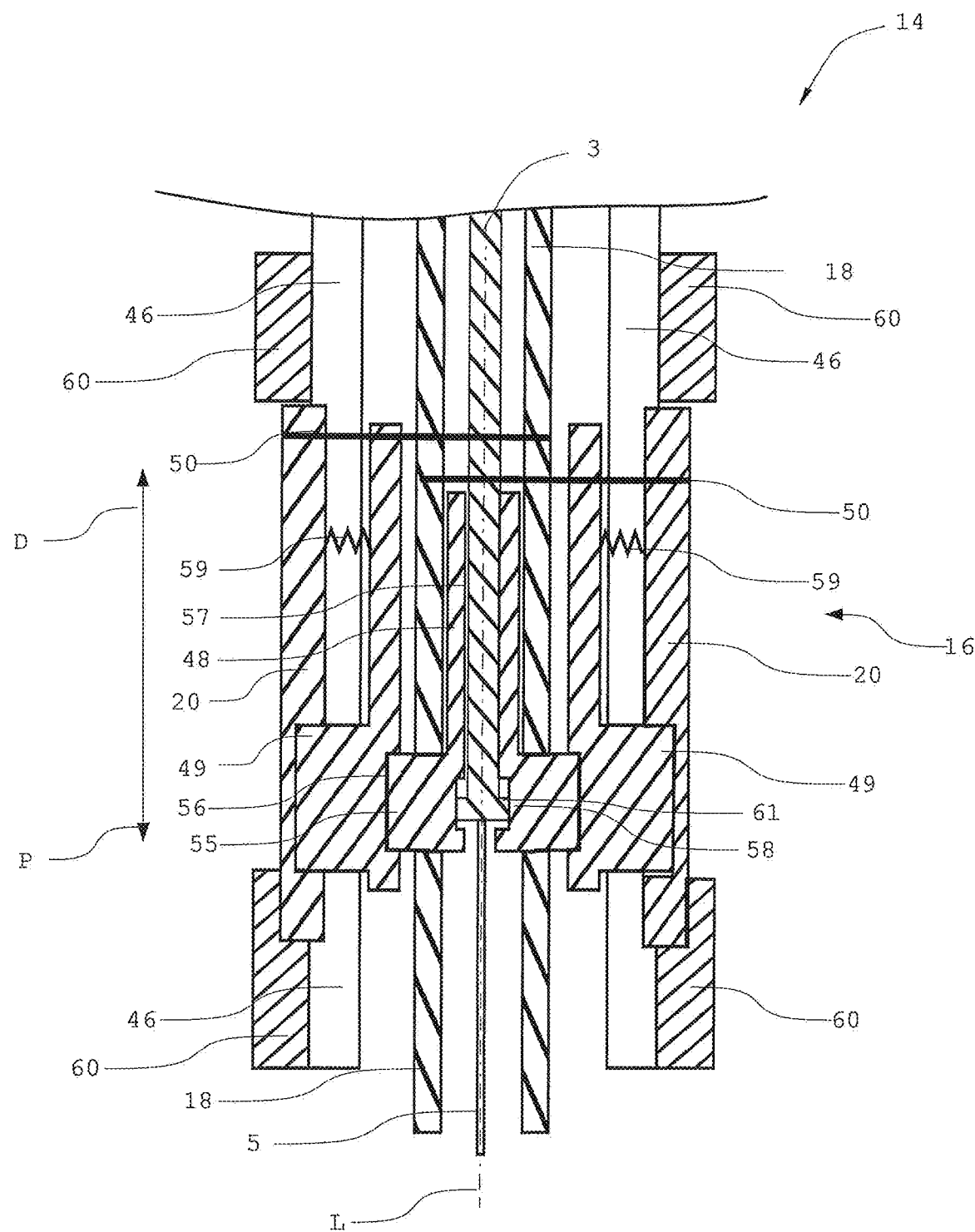
Figure 11:
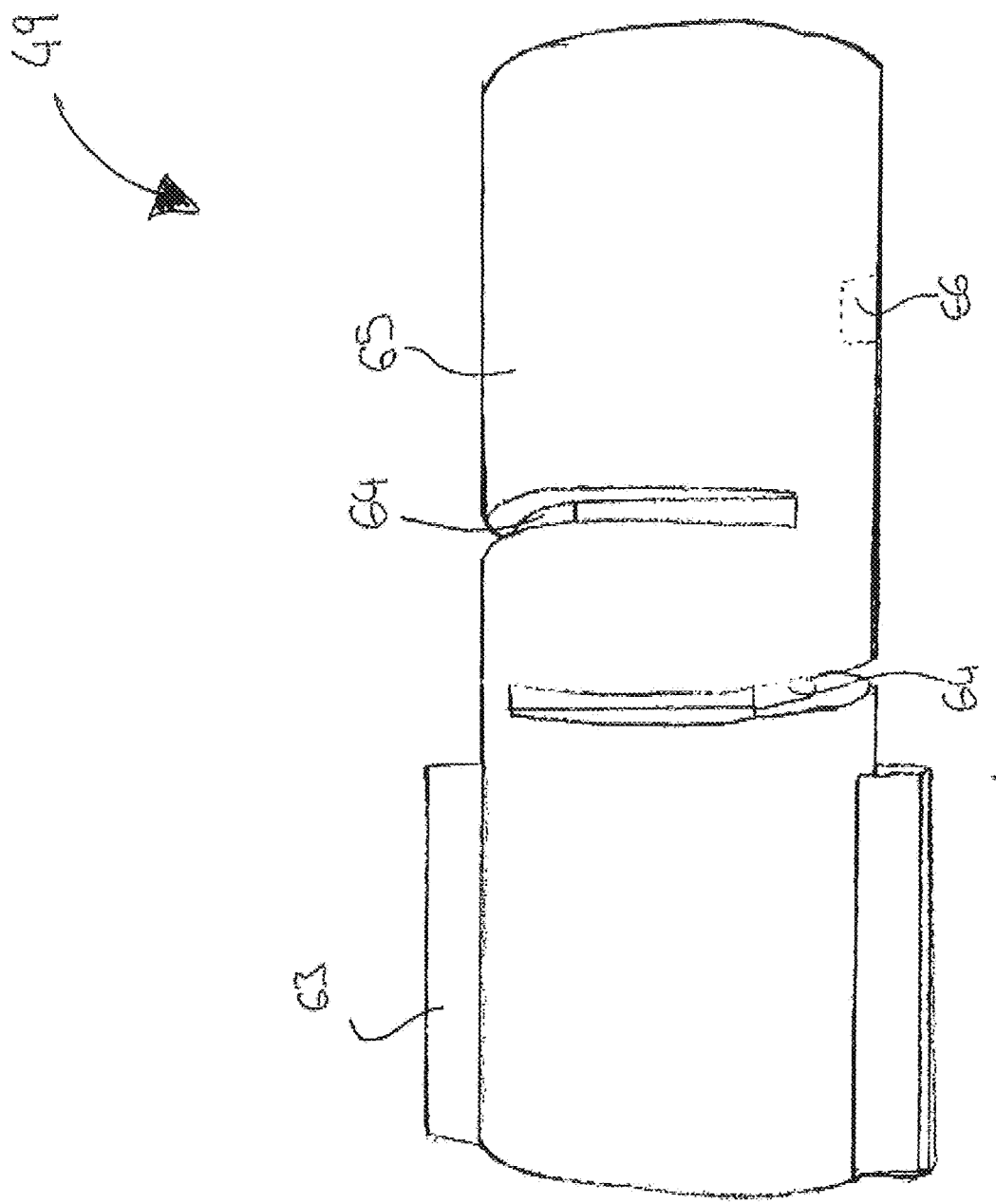
Figure 12:
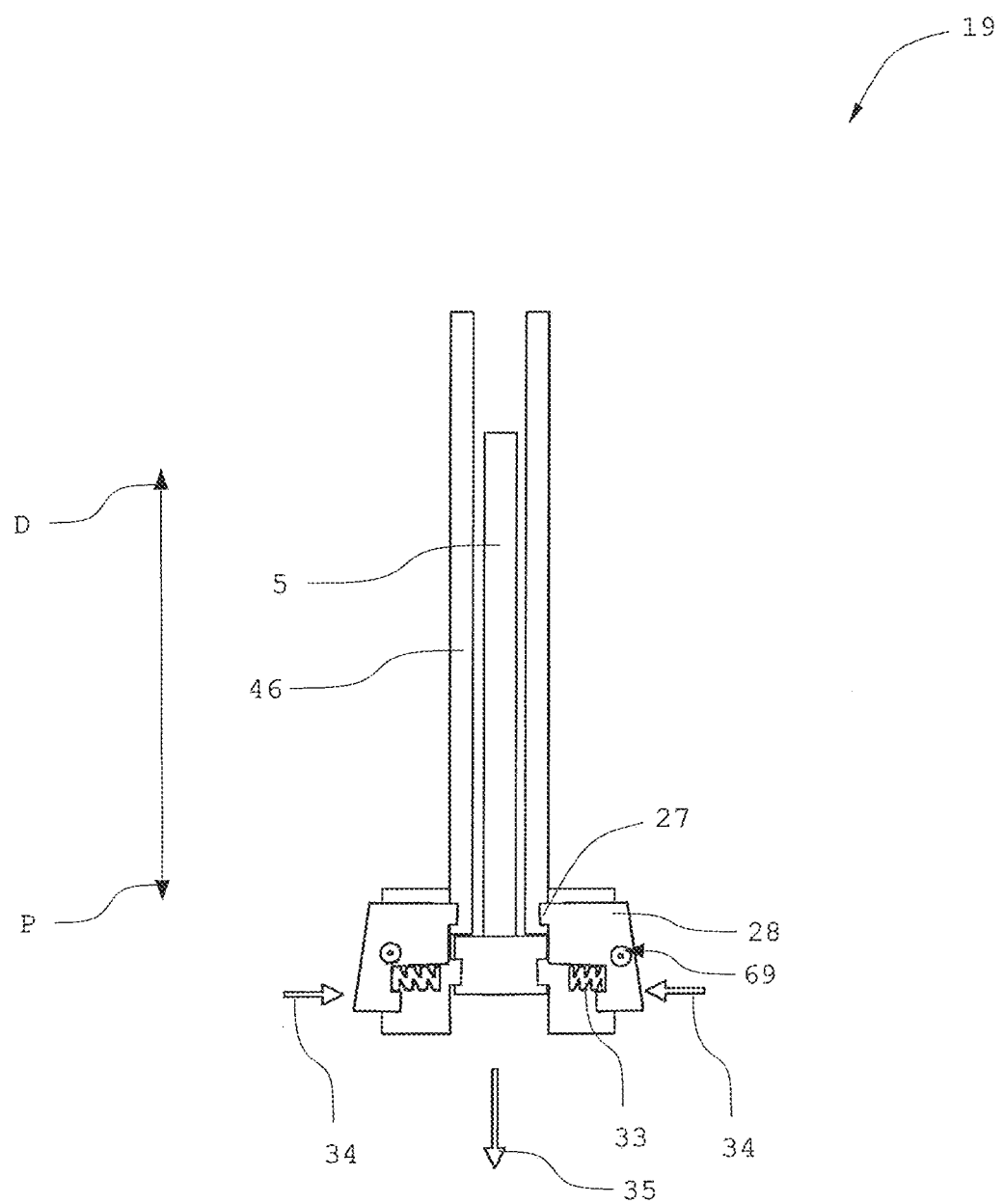
Figures 13A, 13B:
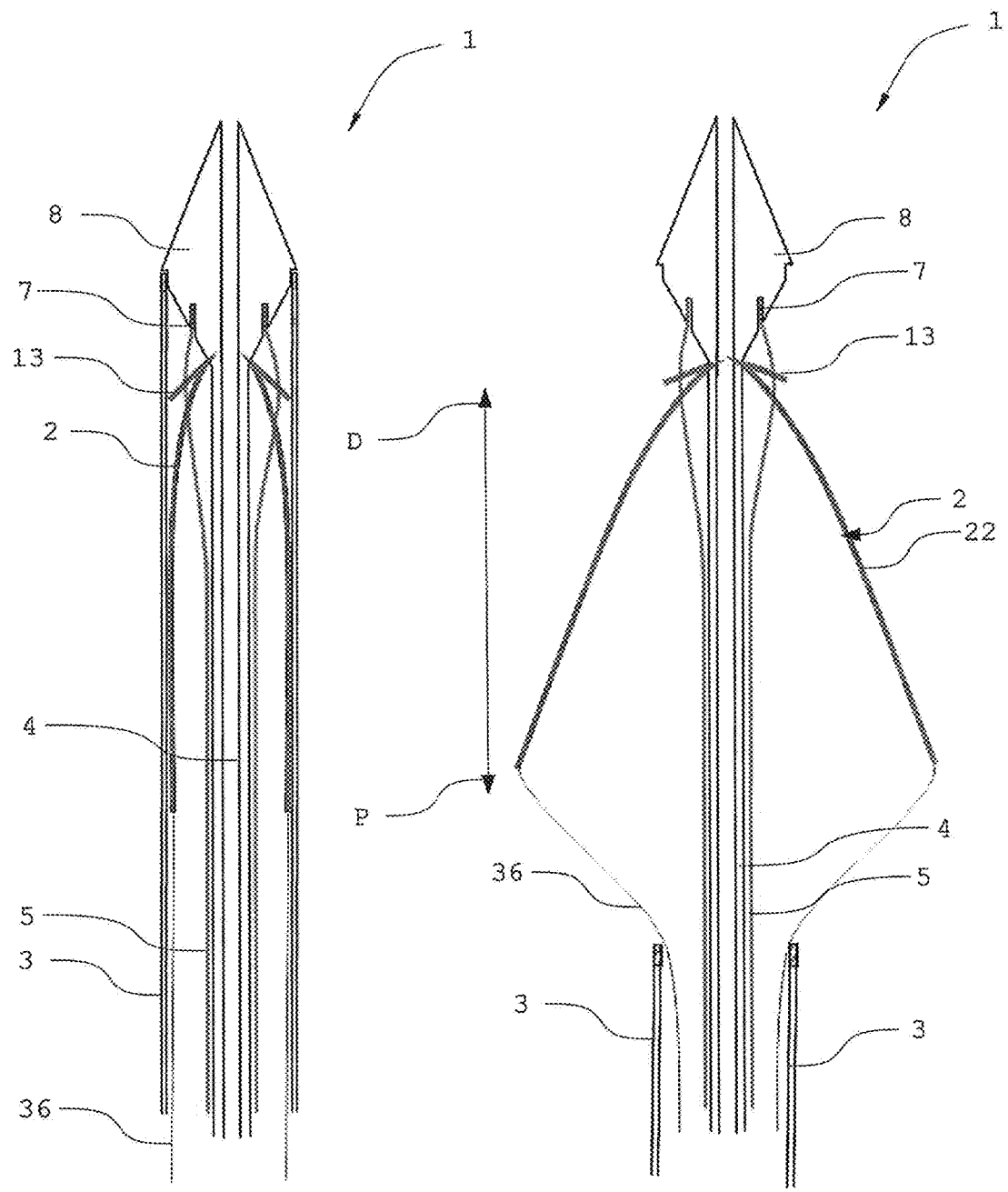
Figures 14A, 14B:
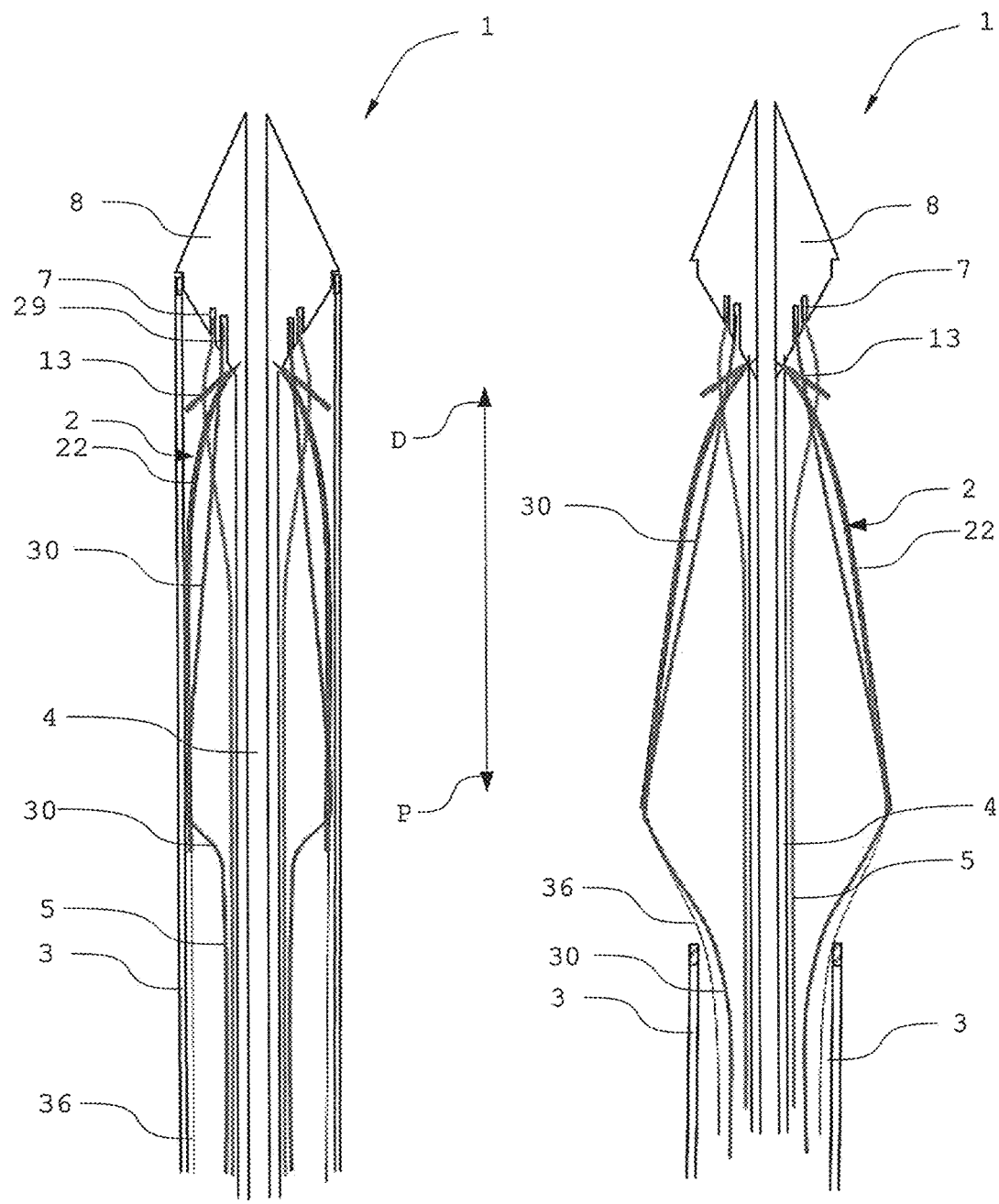
Figure 15A:
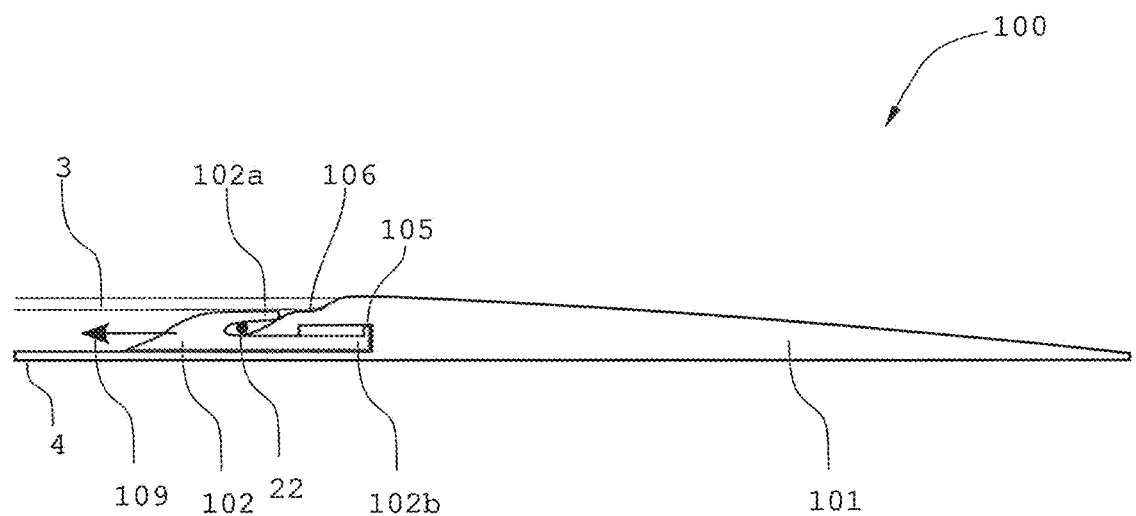
Figure 15B:
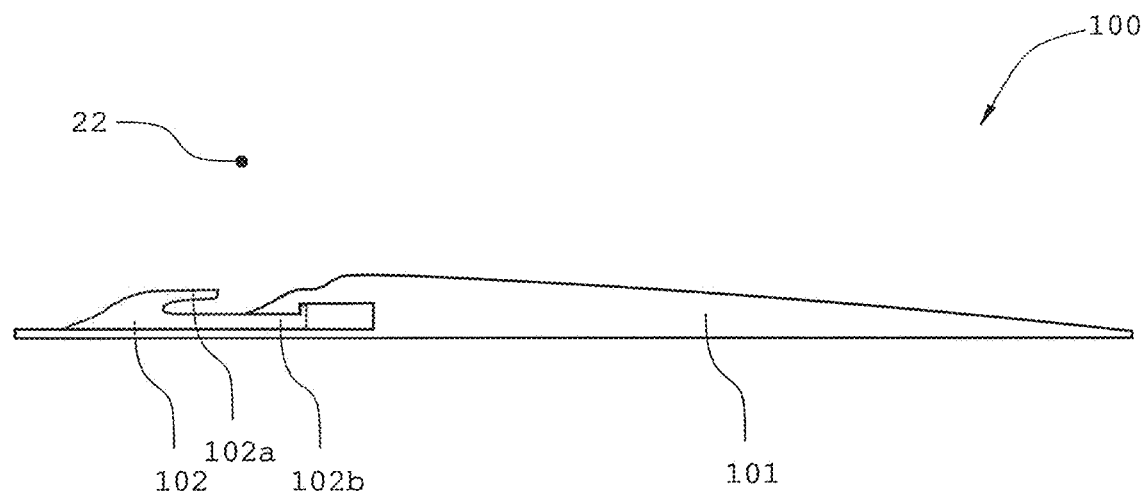
Figure 16A:
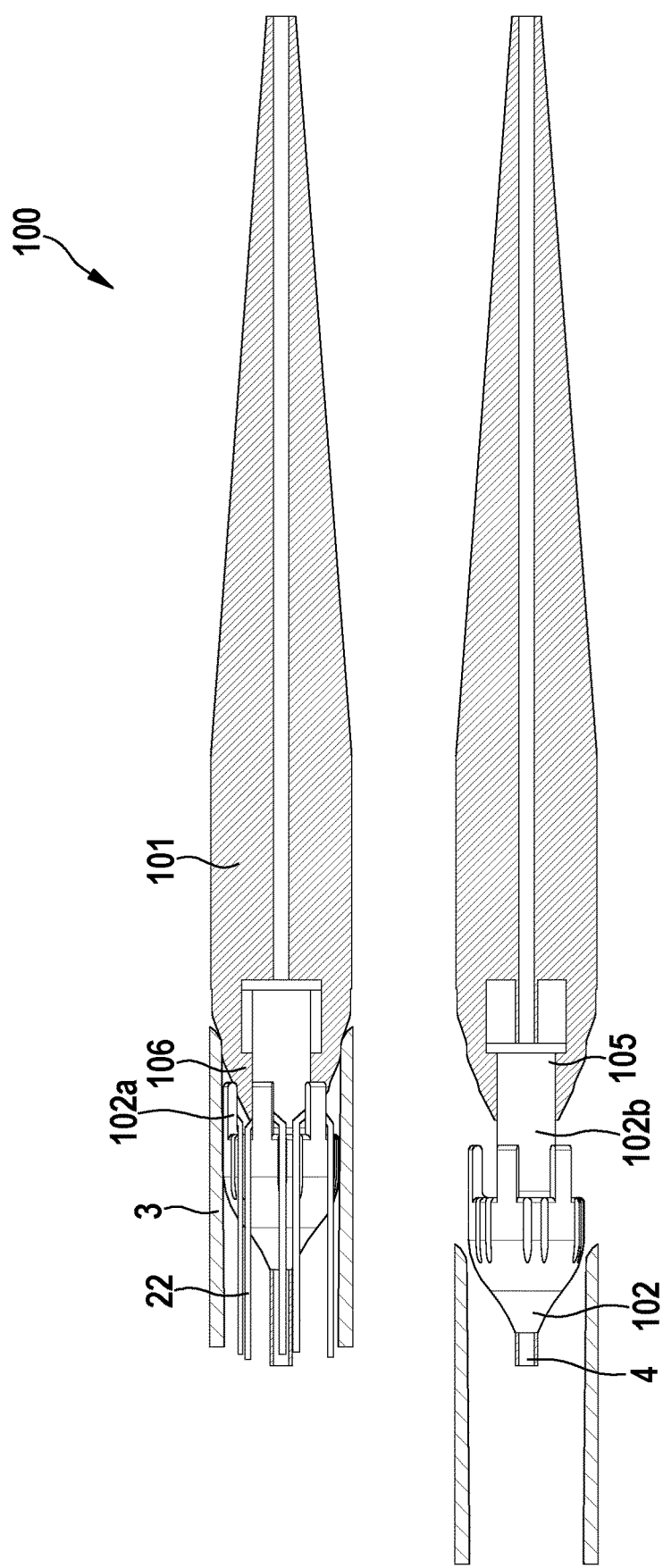
Figure 16B:
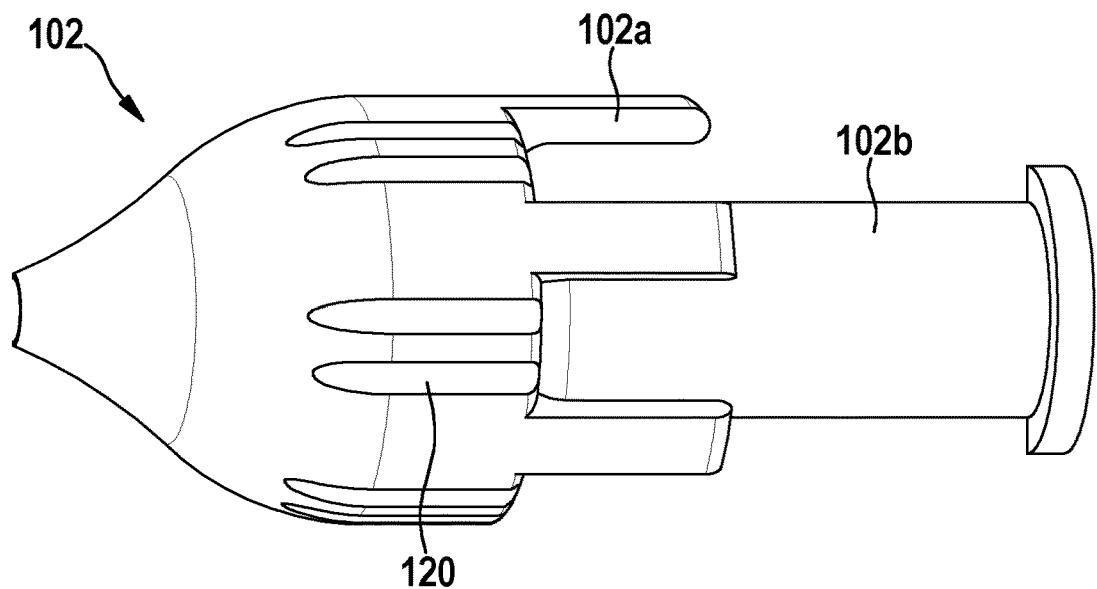
Figure 16C:
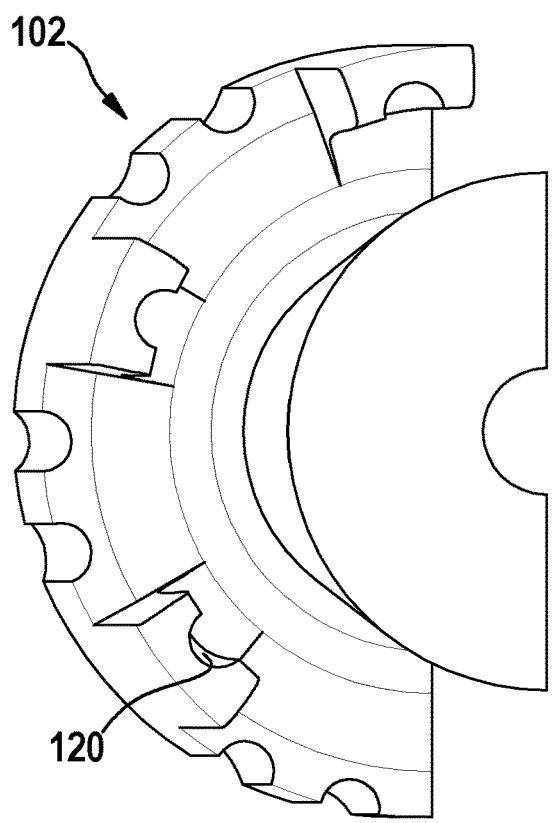

FIG. 6: is a schematic drawing of a handle portion of a delivery device according to the invention;

FIG. 7: is a second view of the delivery device according to FIG. 6;

FIG. 8: is a schematic drawing of a first embodiment of the handle portion;

FIG. 9: is a cross-section of a second embodiment handle portion;

FIGS. 10A and B: are schematic drawings of an inner connecting member;

FIG. 11 is schematic drawing of an outer connecting member;

FIG. 12: is a schematic drawing of a release mechanism;

FIGS. 13A and 13B are schematic drawings of a deployment of an endoprosthesis with a first delivery device;

FIGS. 14A and 14B: are schematic drawings of a deployment of an endoprosthesis with a second delivery device;

FIGS. 15A and 15B: are schematic drawings of a second embodiment of a distal portion of the delivery device; and FIGS. 16A to 17: are further schematic cross-sectional and perspective views of the distal portion of the delivery device shown in FIGS. 15A and 15B.

Figure 1:
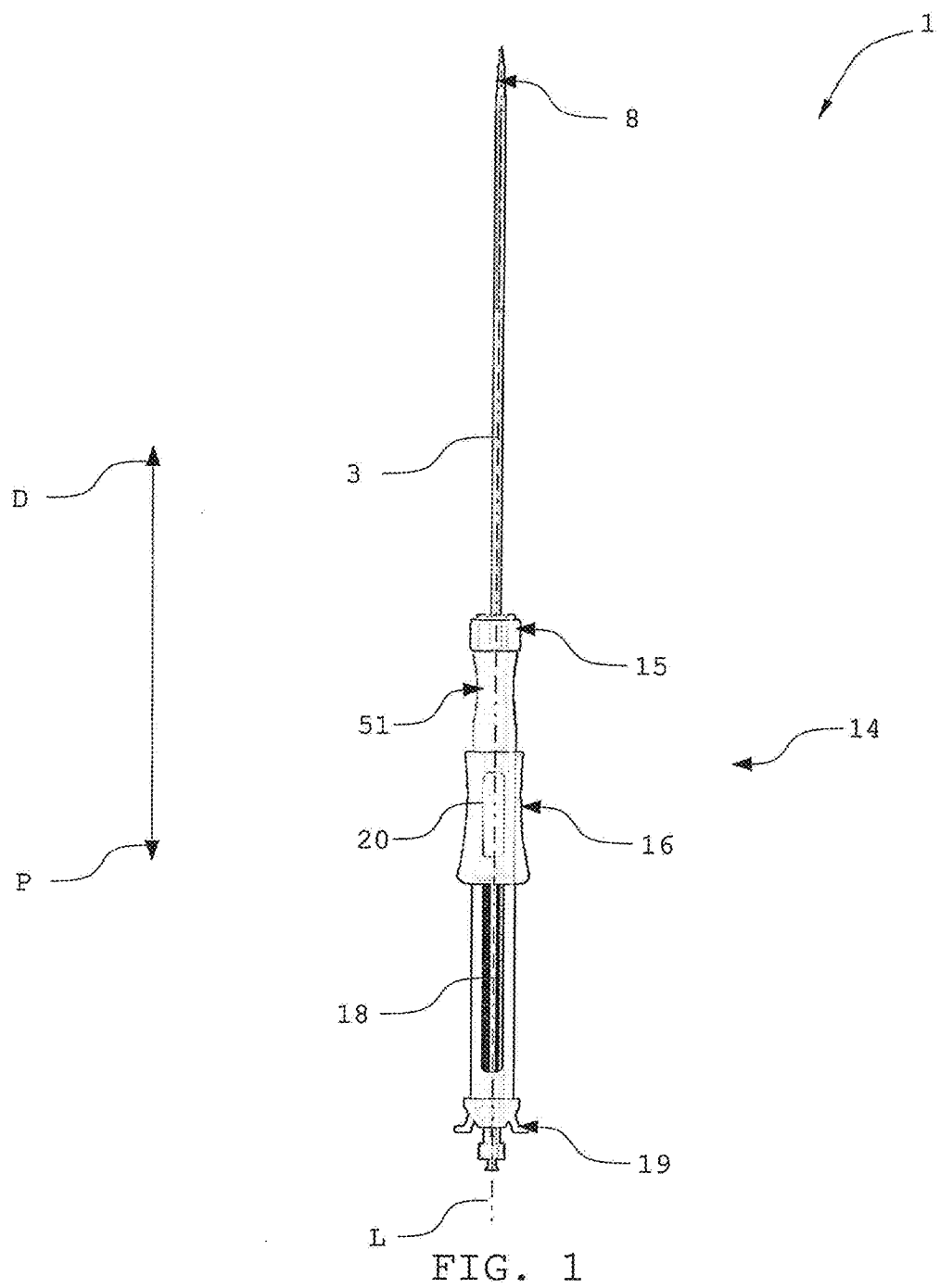

FIG. 1 shows a delivery device 1. The delivery device 1 comprises a distal tip 8 and a handle portion 14. An operator, for example a medical professional, holds the device 1 at the handle portion 14. The direction proximal P and distal D are defined from the perspective of the operator. The handle portion 14 comprises a first gripping portion 15 and a second gripping portion 16.

Further, the handle portion 14 comprises a third gripping portion 51. An outer sheath 3 extends in the distal direction from the handle portion 14. The first gripping portion 15 is ring shaped, rugged on its outer surface and allows the operator to retract the outer sheath 3 slowly. Therefore, the first gripping portion 15 is rotated around a longitudinal axis L of the delivery device. Thereby, the outer sheath 3 is slowly retracted. The outer sheath 3 is made of a sandwich structure of PTFE and metal coils.

As the first gripping portion 15 is rotated the second gripping portion 16 slowly moves in the proximal direction. If the operator wants to retract the outer sheath 3 faster, the operator may press a selection button 20 to decouple the second gripping portion 16 from the first gripping portion 15. The outer sheath 3 can then be retracted by pulling the second gripping portion 16 proximally. Once the selection button 20 is pushed, the second gripping portion 16 is decupled from a threaded tube 18. The selection mechanism is explained later in detail with reference to FIG. 9. Further, the delivery device 1 comprises a release mechanism 19, which is explained in detail with reference to FIG. 12. Further details of the mode of operation are also discussed with reference to FIGS. 6 and 7.

Figure 2:
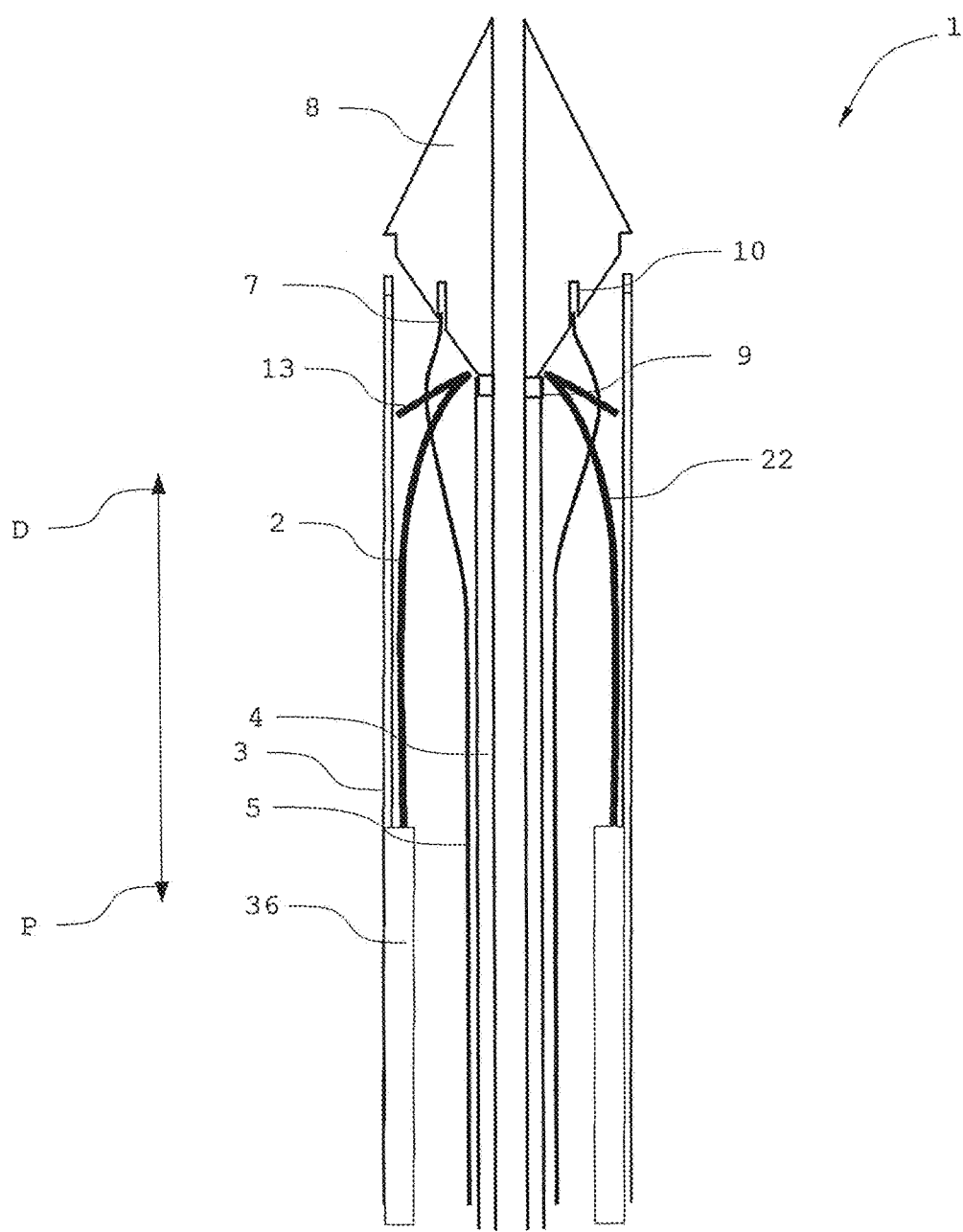

FIG. 2 shows a detailed view of a cross section of a distal part of the delivery device 1. An endoprosthesis 2 is loaded in the delivery device 1. The endoprosthesis 2 is held in a compressed configuration within the delivery device 1 by the outer sheath 3. The outer sheath 3 extends from the handle portion 14 to the distal tip 8. An inner tube 4 is disposed coaxially within the outer sheath 3 and its proximal end is connected to the handle portion 14. At its distal end 9, the inner tube 4 is connected to the distal tip 8. The distal tip 8 and the inner tube 4 are made of Pebax.

The endoprosthesis 2 comprises a stent 22. At a proximal end of the stent 22 an anchor pin 13 is arranged. With regard to the endoprosthesis 2, the directions proximal and distal are defined with regard to a patient, in which the endoprosthesis 2 is implanted. Thus, the directions proximally and distally, when referring to the endoprosthesis 2 are defined opposite to the directions with regard to delivery device in these figures.

Further, the delivery device 1 comprises a restraining tube 5. The restraining tube 5 is disposed between the inner tube 4 and the outer sheath 3. The restraining tube 5 is laced through arches of the stent 22 of the endoprosthesis 2 at a proximal end of the endoprosthesis 2. At its distal end 7, the restraining tube 5 is held in a first recess 10 of the distal tip 8. The first recess 8 extends circumferentially around the distal tip 8 and is located at a proximal side of the distal tip 8.

The distal end 7 of the restraining tube 5 is engaged in the first recess 10. Since it is held in the first recess 10, the endoprosthesis 2 is prevented from disengaging. The restraining tube 2 thus holds the stent 22 in a compressed configuration even when the outer sheath 3 is withdrawn. In the compressed configuration, the stent 22 may be delivered to an implant site and released there into an expanded configuration. A distal portion of the endoprosthesis 2 is held in the delivery device by the outer sheath 3. The distal portion is a graft 36. To release the endoprosthesis 2, first the outer sheath 3 is withdrawn. The endoprosthesis 2 will then partly expand but is kept in a partly compressed configuration by the restraining tube 5. To fully release the endoprosthesis 2, the restraining tube 5 is withdrawn, first out of engagement with the recess 10 and then through the apex of the stent 22.

FIGS. 3A and 3B show the restraining tube 5 in detail. The restraining tube 5 comprises a shaft 25. Five elongations 6 extend from the distal end of the shaft 25. These elongations 6 extend in a distal direction of the delivery device 1. The elongations 6 include distal ends, which form the distal end 7 of the restraining tube 5. The distal ends 7 of the elongations 6 are inserted into the first recess 10 (see FIG. 2). Further, each elongation comprises a slot 12. The slot 12 extends from the distal end 7 of the elongations 6 in a proximal direction. The slots 12 have a length of about 10 mm.

The slots 12 form an attachment element 11. The slots 12 are adapted receive the anchor pin 13 of the stent 22 in a loaded configuration (see FIG. 2). Thereby, the stent 22 is held securely in place. The slot 12 divides a distal portion of the elongations into two fingers 26. Each slot receives one anchor pin 13 of the stent 22. To release the anchor pins 13 from engagement with the restraining tube 5, the restraining tube 5 is simply retracted in a proximal direction. During the retraction, the elongations 6 are first disengaged from first recess 10 and then disengaged from the anchor pins 13. A proximal part of the endoprosthesis 2 is therewith released from the delivery device 1 and allowed to fully expand.

Figures 4A, 4B:
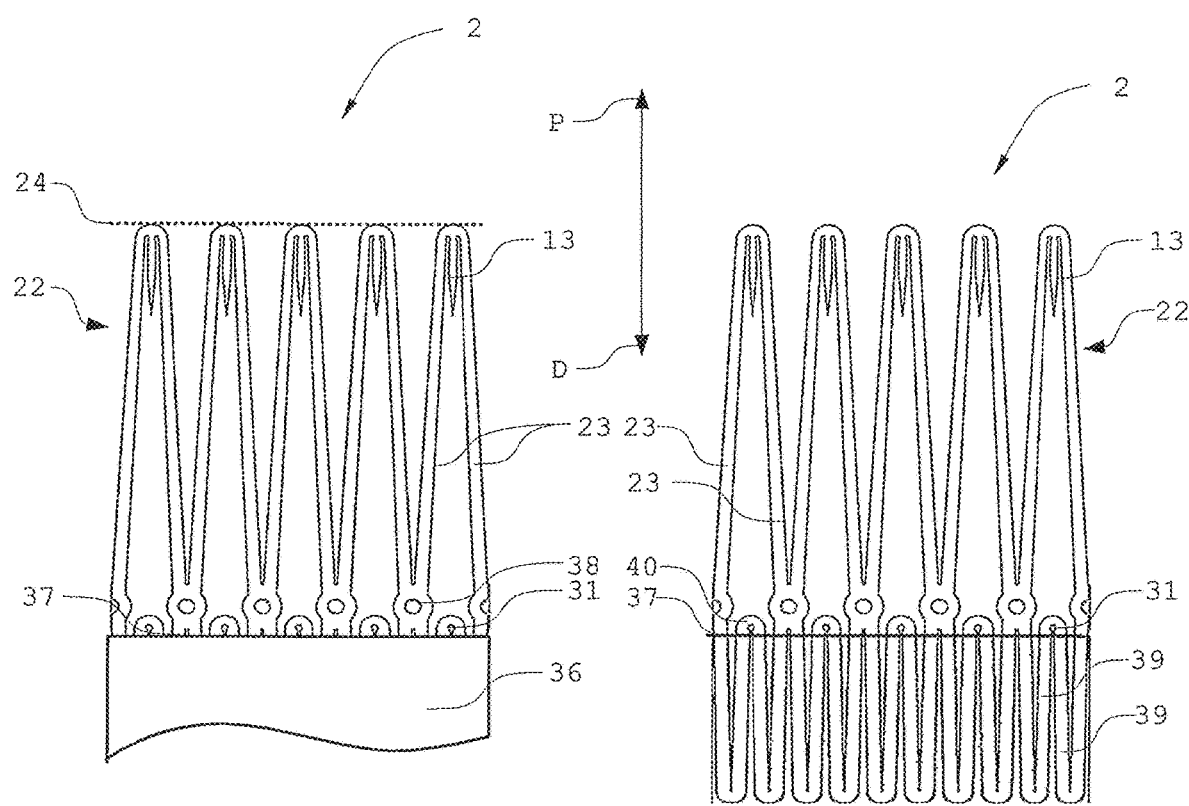
FIGS. 4A and 4B are schematic drawings of a proximal part of a stent graft according to the invention.

FIGS. 4A and 4B show a proximal portion of the endoprosthesis 2. The endoprosthesis 2 comprises the stent 22 and the endoluminal graft 36. The pins 13 are disposed at a proximal end 24 of the stent 22. Struts 23 extend from the proximal end 24 of the stent 24. The Struts 23 extend in a longitudinal direction of the stent 22. Two struts 23 meet at an apex, where one anchor pin 13 is arranged. Thus, the struts 23 form arches. The stent 22 of FIGS. 4A and 4B comprises five such apexes, each with one anchor pin 13. The slots 12 (see FIGS. 3A and 3B), receive the pins 13, when the stent is loaded in the delivery device 1.

In a distal direction the struts 23 meet with neighbouring struts. At the point where the arches meet, a hole for radiopaque markers 38 is formed. A loading hole 31 is arranged distally from the markers 38. The endoluminal graft 36 and its proximal edge 37 are arranged even further distally. An undulating structure is by struts 39, which extend from the radiopaque markers 38. The loading hole 31 is disposed distally of and in between two radiopaque markers 38 along a circumferential direction. The loading hole 31 is formed within an apex 40 of two proximally extending struts 39. The hole 31 comprises an open end in a distal direction. When the stent is loaded into the delivery device 1 a wire is laced through the loading hole 31 and then the wire is used to pull the stent through a conically tapering hole. Thereby, the stent is compressed and may be inserted into a delivery device.

Figure 5:
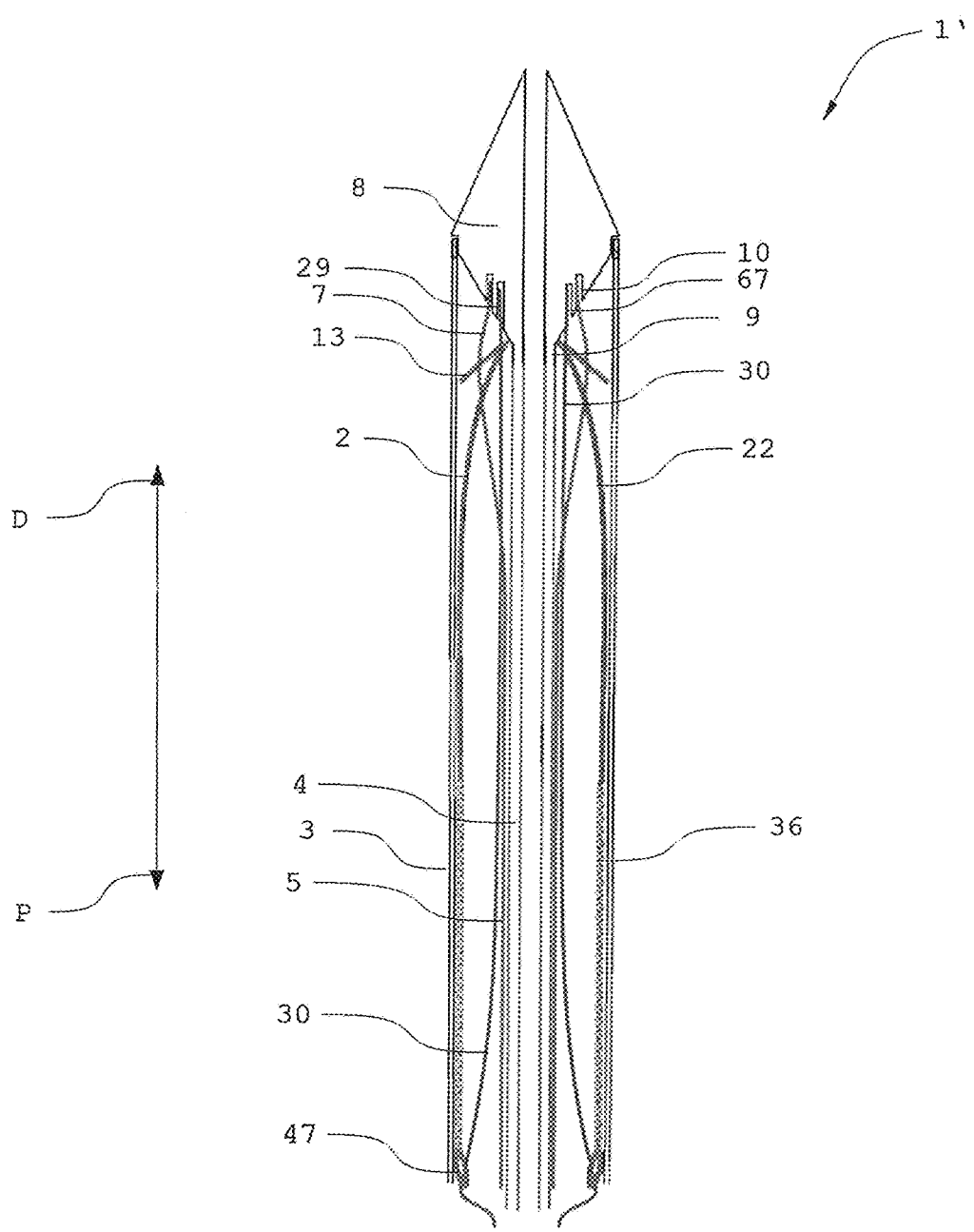
FIG. 5 is a detailed view of a second embodiment of a distal portion of a delivery device according to the invention.

FIG. 5 shows a second embodiment of a delivery device 1'. The delivery device 1' is similar to the delivery device 1. In contrast to the delivery device 1 shown in FIG. 2, the delivery device in FIG. 5 comprises a second restraining tube 30. The second restraining tube 30 is shaped like the first restraining tube 5 (see FIGS. 3a and 3b). However the second restraining tube 30 does not include slots 12 and its elongations are longer than the ones 6 of the first restraining tube 5. The elongations of the second restraining tube 30 are laced through repositioning holes 47 of the endoprosthesis 2.

Distal ends 67 of the elongations of the second restraining tube 30 are held in a second recess 29 of the distal tip 8. The second recess 29 is also arranged on a proximal side of the distal tip 8 and extends circularly around the distal tip 8. As can be seen in FIG. 5, repositioning holes 47 are disposed at a distal part of the endoprosthesis 2. Thus the elongations of the second restraining tube 30 extend at least from the repositioning hole 47 to the distal tip 8. The repositioning holes 47 are arranged distally of the stent 22 and in a proximal part of the graft 36. FIG. 5 only shows a part of the graft 36. The graft 36 extends further in the distal direction of the endoprosthesis 2.

A proximal part of the second restraining tube 30 is disposed between the first restraining tube 5 and the outer sheath 3. The elongations of the second restraining tube 30 are disposed in the radially inward second recess 29. Thereby, the second restraining tube does not hold the stent 22 compressed but a more distal portion of the endoprosthesis.

FIG. 6 shows the handle portion 14 in detail. The handle portion 14 comprises a body 46, the first gripping portion 15, the second gripping portion 16 and a third gripping portion 51. The third gripping portion 51 is part of the body 46 and does not take part in the withdrawal of the outer sheath 3. The first gripping portion 15 is arranged distally to the second and third gripping portions 16, 51. The first griping portion 15 is a ring with a rugged surface. Thereby, the operator can securely grip the first gripping portion 15. The body 46 comprises a first slotted hole 54 and a second slotted hole 54 on an opposite circumferential side. The slotted holes 54 extend along an axial direction of the handle portion 14. Within the slotted hole 54, the threaded tube 18 can be seen. Further, the tube 18 also comprises two axial extended slotted holes 41.

FIG. 7 shows a second view of the handle portion wherein a distal part of the handle portion is seen in a cross section. Within the hollow body 46 an inner cylinder 42 is arranged. The inner cylinder 42 is integrally formed with the first gripping portion 15 and connected to the threaded tube 18. The connection between the threaded tube 18 and the inner cylinder 42 and thus the first gripping portion 15 is fixed. Alternatively all parts, of threaded tube 18 in the cylinder 42 and first gripping portion 15 may be integrally formed. Thus, upon rotating the first gripping portion 15, the threaded tube 18 is also rotated around the axis of the handle portion. As can be seen from FIG. 7 the release mechanism 19 comprises a release lever, realized as arm 28.

FIG. 8 shows a schematic drawing of functional principle of a first embodiment of the handle portion 14'. A first gripping portion 15' is ring shaped and comprises an inner threading 17. The inner threading 17 is in operable connection with a threaded tube 18'. When the first gripping portion 15' is rotated, the threaded tube 18' is moved in a proximal direction. A second gripping portion 16' is releasably connected to the threaded tube 18'. The second gripping portion 16' is fixedly connected to an outer sheath 3' with a link 43. When the threaded tube 18' is moved, the second gripping portion 16' is also moved and the outer sheath 3' is ultimately retracted.

The second gripping portion 16' may be coupled the first gripping portion 15' with a wire 50 (see FIG. 9). When the second gripping portion is released from the threaded tube 18', the outer sheath 3' may be retracted by pulling the second gripping portion 16'.

A second embodiment of the handle portion 14 is described in detail with reference to FIGS. 9, 10 and 11. FIG. 9 shows a cross section of the handle portion 14 and the second gripping portion 16. A socket 60 is arranged on the body 46. The socket 60 holds the button 20 for releasing the second gripping portion 16 from the first gripping portion 15. The second gripping portion 16 further comprises an outer connecting member 49 (see also FIG. 11). Wires 50 are fixedly attached to the buttons 20 and engage the threading of the threaded tube 18. The wires 50 have a U-shape and enclose the threaded tube 18.

FIG. 11 shows a perspective view of the outer connecting member 49. The outer connecting member 49 comprises a tubular body 65. The button 20 is connected to the outer connecting member 49 with a spring 59 (see FIG. 9). The spring 59 is attached to the outer connecting member 49 in a recess 66. The recess 66 holds the spring 59 with a friction fit. When an operator presses the button 20, the spring 59 is compressed and the button 20 is moved radially inwardly at least at a distal portion of the button 20 and the wires 50 are disengaged from the threading of the threaded tube 18. The outer connecting member 49 comprises cams 63, which extend radially outwardly. The buttons 20 are mounted on the cams 63. Further, the outer connecting member comprises through holes 64. The wires 50 are arranged in the through holes 64. A bottom part of the U-shape is disposed in the through hole 64, while both ends of the U-shape of each wire 50 are attached to one button 20. The threaded tube 18 engages the bottom part of the U-shape.

As described with reference to the FIG. 7, upon rotation of the first gripping portion 15, the threaded tube 18 is rotated. The button 20 is operatively engaged to an outer threading of the threaded tube 18 with two wires 50 (see FIG. 9).

Returning to FIG. 9, the wires 50 extend through the through holes 64 of the outer connecting member 49. When the threaded tube 18 is rotated, the wires 50 slip along a thread of the threaded tube 18. Thereby, the wires 50 move the second gripping portion along the axial direction of the handle portion 14.

When the button 20 is pushed radially inwardly the wires 50 are disengaged from the threading of the threaded tube 18, as they are moved out of threads of the threaded tube 18. Then, the second gripping portion 16 can be moved independently of the threaded tube 18 and the first gripping portion 15. The movement in the axial direction of the second gripping portion 16 is transferred by an inner connecting member 48 (see FIG. 10) to the outer sheath 3. The inner connecting member 48 comprises a tubular body 62. The outer sheath 3 can be retracted faster with the second gripping portion 16 after pushing the button 16.

At a proximal portion of the outer sheath 3, the outer sheath 3 comprises cams 61. The cams 61 are located in a circumferential recess 58 of an inner lumen 57 of the inner connecting member 48 (see also FIG. 10B). The recess 58 allows a transfer of axial forces from the inner connecting member 48 to the outer sheath 3 over the cam 61, and allows the inner connecting member 48 to rotate relatively to the outer sheath 3.

Figure 10:
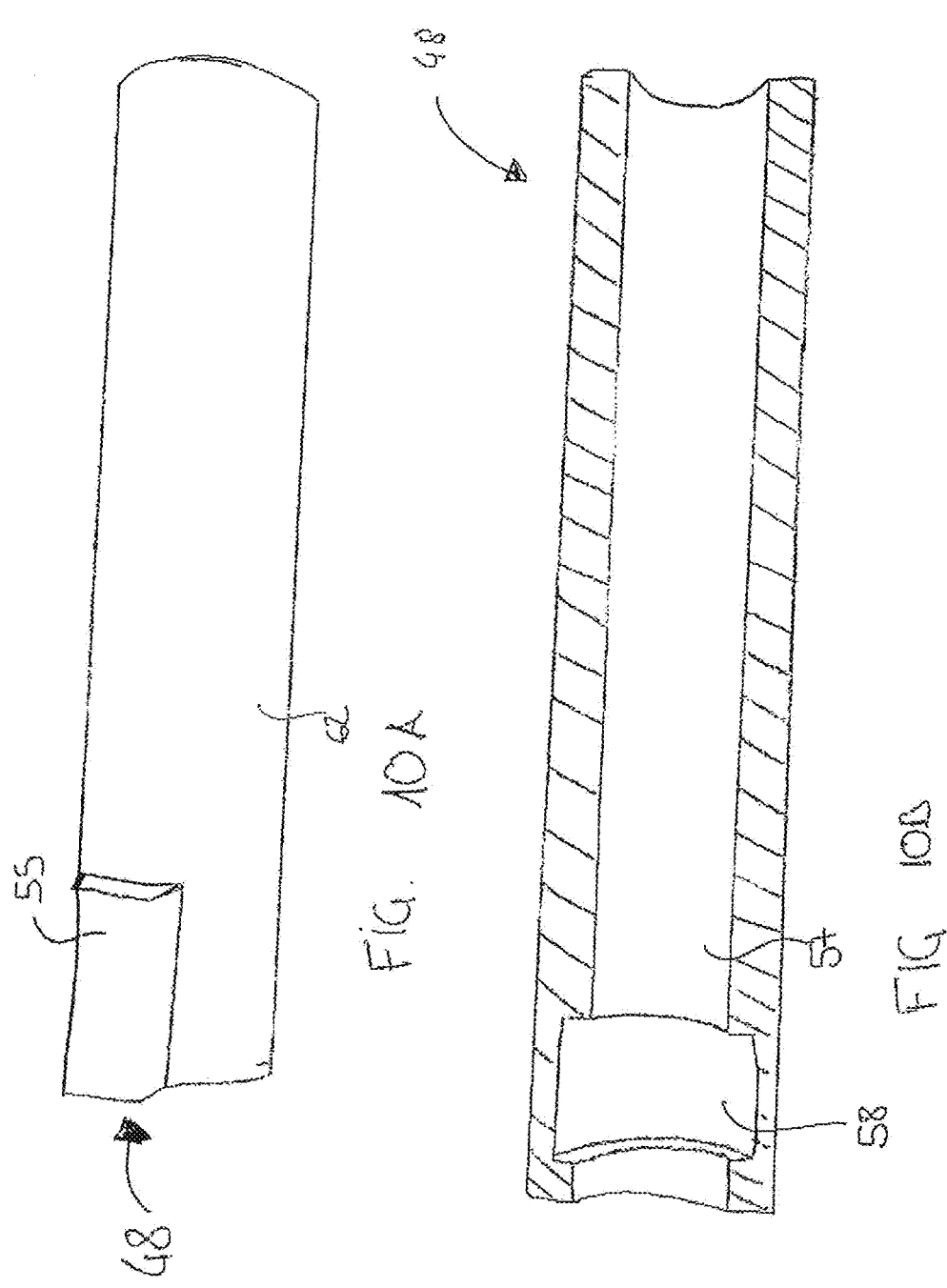

FIG. 10A shows a perspective view of the inner connecting member 48 and FIG. 10B shows a perspective view of a cross-section of the inner connecting member 48. As can be seen in the FIGS. 9 and 10, the tubular body 62 comprises the inner lumen 57. The outer sheath 3 extends through the inner lumen 57 of the inner connecting member 48. Within the outer sheath 3 the restraining tube 5 is arranged (see FIG. 9). The restraining tube 5 extends through the second gripping portion to a proximally disposed release mechanism 19 (see FIG. 12).

Additionally the inner connecting member 48 comprises cams 55, which extend radially outwardly. The cams 55 engage a circular recess 56 of the outer connecting member 49.

When the first gripping portion 48 and thus the threaded tube 18 are rotated, the inner connecting member 48 is rotated as well, as the cams 55 extend through the axially slotted holes 41 of the threaded tube 18. The outer sheath 3 however, is not rotated, as the rotary motion is not transferred from the inner connecting member 48 to the outer sheath 3 because of the circumferential recess 58. The rotary motion is neither transferred to the second gripping portion 16 because of the recess 56. The recess 56 only transfers axial forces from the second gripping portion to the inner connecting member and its cams 55.

As can be seen from FIG. 9, a cut-out in the socket 60 is shorter in axial direction than a length of the button 20 in axial direction. Thus, a proximal portion of the button 20 is fixated to the handle portion by the socket 60. The distal portion is held by the wire 50. The spring 59 pushes the button 20 radially outward. This pushes the wire 50 into the threading of the tube 18. Hence, at the same time the outer threading of the tube 18 provides a stop for the button at its distal part.

FIG. 12 shows schematic drawings of the release mechanism 19. In the locked position the first restraining tube 5 is fixedly attached to the body 46. The connection is formed by a lever realized as an arm 28. The arm 28 comprises a nose 27, which engages a recess in the body 46. The arm 28 is held at a pivot 69. The arm 28 is rotatable around pivot 69. On the opposite of pivot 69 a spring 33 is arranged. The arm may also biased by two springs at each end of the arm. The spring 33 biases the arm 28 with its nose 27 into the recess of the body 46. When the operator actuates the arm 28—as indicated by arrows 34—and presses against the spring force, the nose 27 is released from the body 46. Then, the restraining tube 5 may be withdrawn in a proximal direction as indicated by arrow 35.

FIGS. 13A and 13B show a deployment of the endoprosthesis 2 with the delivery device 1 with a handle portion 14. FIG. 13A shows the endoprosthesis 2 in a compressed configuration (see FIG. 2). FIG. 13B shows the endoprosthesis 2 in a partially expanded configuration. When the operator is at the desired implantation site, the operator starts withdrawing the outer sheath 3 with the first gripping portion 15. As the outer sheath 3 is withdrawn, a portion of the endoprosthesis 2, which is arranged distally of the pins 13, i.e. the graft 36 and a distal part of the stent 22, starts expanding. However, while retracting the outer sheath 3, the proximal end 24 of the endoprosthesis 2 with its pins 13 is still held in a partially compressed configuration by the restraining tube 5. Thus, the endoprosthesis 2 and stent 22 are not anchored to a native vessel wall. The operator may still reposition the endoprosthesis 2, if desired.

In particular, the operator may push the endoprosthesis 2 in its proximal direction for repositioning. Once the operator is satisfied with the position the restraining tube 5 may be withdrawn and thus the stent 22 is released and the anchor pins 13 are deployed. The anchor pins 13 may then engage the vessel wall (not shown) to anchor the endoprosthesis 2.

FIGS. 14A and 14B show a deployment of the endoprosthesis 2 with two restraining tubes 5, 30. In contrast to the embodiment shown in FIG. 5, the second restraining tube 30 holds a distal portion of the stent 22. The endoluminal graft 36 is thus deployed before the stent 22. The stent 22 is also held in a partially compressed configuration by the second restraining tube 30. In this partially expanded configuration the stent 22 and the graft 36 may be repositioned.

The repositioning in the embodiment of FIGS. 14A and 14B is easier, because the endoprosthesis is not fully in contact with a native vessel wall. The position of the stent 22 can be found more easily, since in particular the distal part of the stent 22 is not in contact with vessel wall. Thereby, an operator can even more easily reposition the stent 22 and a corresponding endoprosthesis 2 as desired. Once the endoprosthesis 2 is at the desired implantation site, the second restraining tube 30 may be withdrawn and the position may be further be adjusted if needed, as described with reference to FIGS. 13A and B. The restraining tube 5 still holds the anchor pins 13 in a compressed configuration. After a retraction of the first restraining tube 5, the pins 13 are deployed in a desired portion. This procedure allows are very precise endoprosthesis 2 placement.

FIGS. 15A to 17 show a cross-sectional views and perspective views of an alternative holding mechanism for the stent 22. In the shown embodiment, the device 100 includes a harpoon member 102. The harpoon member 102 has a tubular shape and is formed as an integral cylindrical unit.

The harpoon member includes on its distal side an arm 102a and a base 102b. The arm 102a extends through an arch of the stent 22, i.e. is laced through the stent 22. A tip 101 of the catheter includes a proximal extension 106. The distal extension closes a gap between the arm 102a and the base 102b in the delivery configuration. As a result, the stent 107 is held securely between the arm 102a, the base 102b and the tip 101. The harpoon member 102 may include one or more recesses 120 for accommodating the struts of the stent 22. The recesses 120 may be arranged in particular on a radially inner side of the arms 102a and/or on a radially outer surface, against which the struts are adapted to be pressed.

The harpoon member 102 may include one or more arms 102a. The base may have tubular form or may be formed as a tab along a part of the circumference.

When the stent is released, first the outer sheath 3 is withdrawn. When the outer sheath 3 is withdrawn, the proximal parts of the stent 22 are expanded and the stent can be positioned as described in detail above. Once the final position for the endoprosthesis 2 is found, the harpoon member 102 is retracted in a proximal direction (see arrow 109). When the harpoon member 102 is retracted, the stent is released from the arm 102a and expands such that the anchor pins 13 (see FIG. 2) engage a wall of a vessel of a patient.

The harpoon member 102 is held slidably within a proximal end of the tip 101. As can be seen from FIGS. 15A to 17, the base 102b includes on its distal end a radial extension formed as flange 105. The proximal extension 106 forms together with the inner tube 4 a cavity. The base 102b is held axially slidably in the cavity. A cross-section of the entry to the cavity is smaller in cross-section than the cavity such that the harpoon member 102 can only travel a set distance. The flange 105 is larger in cross-section than the entry. Thereby, the walls of a vessel of a patient are protected from edges of the extension 106 and the harpoon member 102 cannot be lost.

A distal side 103 of the harpoon member 102 is inclined. Preferably, the edges on the distal side 103 are rounded and the inclination is below 45°. Thereby, when the catheter is retracted after the placement of the endoprosthesis 2, the walls of a vessel are not damaged by the distal side of the tip.

The invention claimed is:

1. Delivery device for an endoprosthesis, comprising an outer sheath,
   an inner tube being arranged within the outer sheath and
   at least one restraining tube for holding the endoprosthesis in a compressed configuration being arranged between the outer sheath and the inner tube,
   wherein the restraining tube is adapted to be located at least partially within the endoprosthesis when holding the endoprosthesis,
   wherein the outer sheath, the inner tube and the at least one restraining tube are coaxial,
   wherein the restraining tube includes at least one axial elongation extending from a distal end portion of the restraining tube, the at least one axial elongation being adapted to be laced through portions of the endoprosthesis; and
   a distal tip attached to a distal end of the inner tube, wherein the distal tip comprises at least one recess, wherein the at least one recess is adapted to receive at least one of the elongation(s) of a restraining tube.

2. The delivery device according to claim 1, wherein at least one restraining tube includes multiple elongations extending from the distal end portion of the restraining tube.

3. The delivery device according to claim 1, wherein the at least one restraining tube is releasably engageable to the distal tip by engagement of at least one its elongation(s) in one of the at least one recess of the distal tip.

4. The delivery device according to claim 1, wherein the device comprises a first and a second restraining tube and in that the distal tip comprises a first recess and a second recess wherein the first recess is adapted to receive at least one of the elongation(s) of the first restraining tube and wherein the second recess is adapted to receive at least one of the elongation(s) of the second restraining tube.

5. The delivery device according to claim 1, wherein at least one of the elongations includes at least one attachment element adapted to be engaged with a corresponding element of the endoprosthesis.

6. The delivery device according to claim 1, wherein a first restraining tube is adapted to be laced through a proximal portion, in particular proximal arches, of the endoprosthesis.

7. The delivery device according to claim 1, wherein a second restraining tube is adapted to be laced through a distal portion of the endoprosthesis.

8. The delivery device according to claim 1, wherein the delivery device comprises a first restraining tube and a second restraining tube.

9. The delivery device according to claim 8, wherein each of the first and the second restraining tubes includes multiple elongations extending from their respective distal end portions, wherein the elongations of the second restraining tube are longer in an axial direction of the restraining tubes than the elongations of the first restraining tube.

10. The delivery device according to claim 8, wherein the first restraining tube is at least partially arranged within the second restraining tube.

11. The delivery device according to claim 1, wherein the elongation(s) comprise or are made of a biocompatible material.

12. A delivery system comprising a delivery device according to claim 1 and an endoprosthesis, wherein the endoprosthesis comprises a stent wherein the elongation(s) of the at least one restraining tube are laced through portions of the endoprosthesis.

13. The delivery system according to claim 12, wherein the stent comprises arches formed by struts wherein elongations of a first restraining tube are laced through the arches of the stent.

14. The delivery system according to claim 12, wherein the endoprosthesis comprises a graft, wherein elongations of a second restraining tube are laced through the graft of the endoprosthesis.

15. The delivery system according to claim 12, wherein the elongations of a first and/or second restraining tube are laced through struts of the stent forming a ring.

16. The delivery system according to claim 12, wherein the elongations of a second restraining tube are laced through a distal part of the endoprosthesis.

17. The delivery system according to claim 12, wherein the stent includes at least one anchor pin and the delivery device includes at least one elongation, wherein at least one of the elongation(s) comprises one or more slots, wherein at least one slot is operatively engaged or engageable with the at least one anchor pin.

18. The delivery system according to claim 17, wherein one or more anchor pins are arranged on an apex of arches of the stent.

19. The delivery system according to claim 12, wherein the endoprosthesis includes an outer cover covering a part of a stent ring and the stent ring comprises at least one repositioning opening wherein an elongation(s) of at least one restraining tube is laced through the at least one repositioning opening.

* * * * *